United States Patent
Rothberg et al.

(10) Patent No.: US 9,681,857 B2
(45) Date of Patent: Jun. 20, 2017

(54) ENDOSCOPIC INSTRUMENTS AND METHODS OF MANUFACTURE

(71) Applicant: Boston Scientific Scimed, Inc., Maple Grove, MN (US)

(72) Inventors: Elliott Rothberg, Westborough, MA (US); William Gil DeMontes, Pembroke Pines, FL (US); James M. Zardeskas, Pascoag, RI (US); David I. Freed, Westborough, MA (US); Michael J. Magill, Northboro, MA (US); Satish Sharma, Randolph, MA (US); Jon Gingrich, Lancaster, PA (US); Edward Boarini, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 210 days.

(21) Appl. No.: 13/899,285

(22) Filed: May 21, 2013

(65) Prior Publication Data

US 2013/0253530 A1 Sep. 26, 2013

Related U.S. Application Data

(63) Continuation of application No. 10/845,108, filed on May 14, 2004, now abandoned, which is a (Continued)

(51) Int. Cl.
*A61B 10/06* (2006.01)
*A61B 17/29* (2006.01)
(Continued)

(52) U.S. Cl.
CPC .............. *A61B 10/06* (2013.01); *A61B 17/29* (2013.01); *A61B 2017/00858* (2013.01);
(Continued)

(58) Field of Classification Search
CPC ....... A61B 10/06; A61B 17/29; A61B 17/122; A61B 2017/2926; A61B 2017/320064; A61B 2017/2939
(Continued)

(56) References Cited

U.S. PATENT DOCUMENTS 1,368,117 A 2/1921 Claude
1,387,781 A 8/1921 Xing et al.
(Continued)

FOREIGN PATENT DOCUMENTS

AU 771184 B2 4/2001
CA 2 387 141 A1 4/2001
(Continued)

*Primary Examiner* — Kathleen Holwerda
(74) *Attorney, Agent, or Firm* — Bookoff McAndrews, PLLC

(57) ABSTRACT

Embodiments of the invention include a medical device with one or more of a variety of features. More particularly, embodiments of the invention relate to endoscopic devices that include one or more features that improve the use of the device. Examples of such features include chamfered edges and corners on, for example, the end effectors, a surface with a controlled finish also on, for example, the end effectors, a jaw with teeth and/or a tang having various configurations, a handle having soft-grip features, and/or an elongate member with varied rigidity. Other examples of such features include a folded portion on, for example, the end effectors and/or a snap-fit clevis assembly.

19 Claims, 21 Drawing Sheets

Related U.S. Application Data continuation-in-part of application No. 10/778,226, filed on Feb. 17, 2004, now Pat. No. 8,469,993.

(60) Provisional application No. 60/479,145, filed on Jun. 18, 2003.

(51) Int. Cl.
*A61B 17/00* (2006.01)
*A61B 17/32* (2006.01)

(52) U.S. Cl.
CPC . *A61B 2017/294* (2013.01); *A61B 2017/2905* (2013.01); *A61B 2017/2939* (2013.01); *A61B 2017/320044* (2013.01); *A61B 2017/320064* (2013.01)

(58) Field of Classification Search
USPC .......... 606/151, 157, 158, 205–207; 600/564
See application file for complete search history.

(56) References Cited

U.S. PATENT DOCUMENTS

| | | |
|---|---|---|
| 2,401,672 A | 6/1946 | Tinnerman |
| 2,668,538 A | 2/1954 | Baker |
| 3,050,578 A | 8/1962 | Huebner |
| 3,644,965 A | 2/1972 | Kahn |
| 3,711,134 A | 1/1973 | Goldberg |
| 3,742,957 A | 7/1973 | White |
| 3,895,636 A | 7/1975 | Schmidt |
| 4,522,206 A | 6/1985 | Whipple et al. |
| 4,712,545 A | 12/1987 | Honkanen |
| 4,721,116 A | 1/1988 | Schintgen et al. |
| 4,763,668 A | 8/1988 | Macek et al. |
| 4,785,825 A | 11/1988 | Romaniuk et al. |
| 4,815,460 A | 3/1989 | Porat et al. |
| 4,815,476 A | 3/1989 | Clossick |
| 4,817,630 A | 4/1989 | Schintgen et al. |
| 4,880,015 A | 11/1989 | Nierman |
| 4,887,612 A | 12/1989 | Esser et al. |
| 4,889,118 A | 12/1989 | Schwiegerling |
| 4,936,312 A | 6/1990 | Tsukagoshi |
| 4,950,273 A | 8/1990 | Briggs |
| 4,953,559 A | 9/1990 | Salerno |
| 5,046,881 A | 9/1991 | Swager |
| 5,052,402 A | 10/1991 | Bencini et al. |
| 5,059,214 A * | 10/1991 | Akopov et al. ............... 606/207 |
| 5,082,000 A | 1/1992 | Picha et al. |
| 5,133,727 A | 7/1992 | Bales et al. |
| 5,133,735 A | 7/1992 | Slater et al. |
| 5,133,736 A | 7/1992 | Bales, Jr. et al. |
| 5,141,424 A | 8/1992 | Christof |
| 5,141,519 A | 8/1992 | Smith et al. |
| 5,152,778 A | 10/1992 | Bales, Jr. et al. |
| 5,152,780 A | 10/1992 | Honkanen et al. |
| 5,159,374 A | 10/1992 | Groshong |
| 5,165,633 A | 11/1992 | Effa et al. |
| 5,170,800 A | 12/1992 | Smith et al. |
| 5,171,256 A | 12/1992 | Smith et al. |
| 5,171,258 A | 12/1992 | Bales et al. |
| 5,172,700 A | 12/1992 | Bencini et al. |
| 5,174,300 A | 12/1992 | Bales et al. |
| 5,176,702 A | 1/1993 | Bales et al. |
| 5,177,838 A | 1/1993 | Rotter |
| 5,178,624 A | 1/1993 | Kyun |
| 5,192,298 A | 3/1993 | Smith et al. |
| 5,203,785 A | 4/1993 | Slater |
| 5,215,101 A | 6/1993 | Jacobs et al. |
| 5,219,357 A | 6/1993 | Honkanen et al. |
| 5,228,451 A | 7/1993 | Bales et al. |
| 5,234,453 A | 8/1993 | Smith et al. |
| 5,238,002 A | 8/1993 | Devlin et al. |
| 5,241,968 A | 9/1993 | Slater |
| 5,258,004 A * | 11/1993 | Bales et al. .................. 606/205 |
| 5,265,840 A | 11/1993 | Gillespie et al. |
| 5,269,804 A | 12/1993 | Bales et al. |
| 5,275,612 A | 1/1994 | Bales, Jr. |
| 5,293,878 A | 3/1994 | Bales et al. |
| 5,295,990 A | 3/1994 | Levin |
| 5,300,087 A | 4/1994 | Knoepfler |
| 5,304,203 A | 4/1994 | El-Mallawany et al. |
| 5,312,400 A | 5/1994 | Bales et al. |
| 5,313,935 A | 5/1994 | Kortenbach et al. |
| 5,314,406 A | 5/1994 | Arias et al. |
| 5,320,636 A | 6/1994 | Slater |
| 5,330,502 A | 7/1994 | Hassler et al. |
| 5,331,971 A | 7/1994 | Bales et al. |
| 5,336,172 A | 8/1994 | Bales et al. |
| 5,336,220 A | 8/1994 | Ryan et al. |
| 5,342,390 A | 8/1994 | Slater et al. |
| 5,350,356 A | 9/1994 | Bales et al. |
| 5,359,993 A | 11/1994 | Slater et al. |
| 5,373,854 A | 12/1994 | Kolozsi |
| 5,374,277 A | 12/1994 | Hassler |
| 5,389,104 A | 2/1995 | Hahnen et al. |
| 5,392,789 A | 2/1995 | Slater et al. |
| 5,394,885 A | 3/1995 | Francese |
| 5,395,364 A | 3/1995 | Anderhub et al. |
| 5,395,369 A | 3/1995 | McBrayer et al. |
| 5,395,375 A | 3/1995 | Turkel et al. |
| 5,395,396 A | 3/1995 | Lindgren et al. |
| 5,396,900 A | 3/1995 | Slater et al. |
| 5,419,339 A | 5/1995 | Palmer |
| 5,429,596 A | 7/1995 | Arias et al. |
| 5,431,645 A | 7/1995 | Smith et al. |
| 5,439,378 A | 8/1995 | Damon |
| 5,443,380 A | 8/1995 | Riehl |
| 5,452,335 A | 9/1995 | Slater et al. |
| 5,454,378 A | 10/1995 | Palmer et al. |
| 5,462,546 A | 10/1995 | Rydell |
| 5,482,054 A * | 1/1996 | Slater .................. A61M 1/0043 600/564 |
| 5,507,296 A | 4/1996 | Bales et al. |
| 5,507,297 A | 4/1996 | Slater et al. |
| 5,509,922 A * | 4/1996 | Aranyi .................. A61B 17/29 606/205 |
| 5,531,755 A | 7/1996 | Smith et al. |
| 5,542,432 A | 8/1996 | Slater et al. |
| 5,549,547 A | 8/1996 | Cohen et al. |
| 5,549,606 A | 8/1996 | McBrayer et al. |
| 5,553,624 A | 9/1996 | Francese et al. |
| 5,558,100 A | 9/1996 | Cox |
| 5,562,102 A | 10/1996 | Taylor |
| 5,569,243 A | 10/1996 | Kortenbach et al. |
| 5,601,599 A | 2/1997 | Nunez |
| 5,603,711 A | 2/1997 | Parins et al. |
| 5,613,499 A | 3/1997 | Palmer et al. |
| 5,636,639 A | 6/1997 | Turturro et al. |
| 5,638,827 A | 6/1997 | Palmer et al. |
| 5,645,075 A | 7/1997 | Palmer et al. |
| 5,647,115 A | 7/1997 | Slater et al. |
| 5,666,965 A | 9/1997 | Bales et al. |
| 5,667,526 A | 9/1997 | Levin |
| 5,674,220 A * | 10/1997 | Fox .................... A61B 18/1442 606/205 |
| 5,681,348 A | 10/1997 | Sato |
| 5,683,359 A | 11/1997 | Farkas et al. |
| 5,683,385 A | 11/1997 | Kortenbach et al. |
| 5,683,388 A | 11/1997 | Slater |
| 5,684,729 A | 11/1997 | Yamada et al. |
| 5,707,392 A * | 1/1998 | Kortenbach .................. 606/207 |
| 5,722,421 A | 3/1998 | Francese et al. |
| 5,741,285 A | 4/1998 | McBrayer et al. |
| 5,743,906 A | 4/1998 | Parins et al. |
| 5,746,216 A | 5/1998 | Turturro et al. |
| 5,746,740 A | 5/1998 | Nicholas |
| 5,762,613 A | 6/1998 | Sutton et al. |
| 5,766,199 A | 6/1998 | Heisler et al. |
| 5,810,876 A | 9/1998 | Kelleher |
| 5,819,738 A | 10/1998 | Slater |
| 5,840,043 A | 11/1998 | Palmer et al. |
| 5,843,000 A | 12/1998 | Nishioka et al. |
| 5,846,240 A | 12/1998 | Kortenbach et al. |
| 5,908,437 A | 6/1999 | Asano et al. |

(56) References Cited

U.S. PATENT DOCUMENTS

| | | |
|---|---|---|
| 5,919,202 A | 7/1999 | Yoon |
| 5,924,977 A | 7/1999 | Yabe et al. |
| 5,951,488 A | 9/1999 | Slater et al. |
| 5,976,130 A | 11/1999 | McBrayer et al. |
| 6,010,532 A | 1/2000 | Kroll et al. |
| 6,024,708 A | 2/2000 | Bales et al. |
| 6,036,656 A | 3/2000 | Slater |
| 6,041,679 A | 3/2000 | Slater et al. |
| RE36,666 E | 4/2000 | Honkanen et al. |
| 6,074,408 A | 6/2000 | Freeman |
| RE36,795 E | 7/2000 | Rydell |
| 6,083,150 A | 7/2000 | Aznoian et al. |
| 6,099,483 A | 8/2000 | Palmer et al. |
| 6,129,683 A | 10/2000 | Sutton et al. |
| 6,139,508 A | 10/2000 | Simpson et al. |
| 6,149,607 A | 11/2000 | Simpson et al. |
| 6,159,162 A | 12/2000 | Kostylev et al. |
| 6,161,263 A | 12/2000 | Anderson |
| 6,190,399 B1 | 2/2001 | Palmer et al. |
| 6,193,671 B1 | 2/2001 | Turturro et al. |
| 6,193,737 B1 | 2/2001 | Ouchi |
| 6,238,414 B1 * | 5/2001 | Griffiths ............ 606/205 |
| 6,261,242 B1 | 7/2001 | Roberts et al. |
| 6,264,617 B1 | 7/2001 | Bales et al. |
| 6,273,860 B1 | 8/2001 | Kostylev et al. |
| 6,283,924 B1 | 9/2001 | Ouchi |
| 6,299,630 B1 | 10/2001 | Yamamoto |
| 6,309,404 B1 | 10/2001 | Krzyzanowski |
| 6,368,290 B1 | 4/2002 | Baska |
| 6,378,351 B1 | 4/2002 | Ouchi et al. |
| 6,402,728 B2 | 6/2002 | Otsubo |
| 6,409,678 B2 | 6/2002 | Ouchi |
| 6,425,910 B1 | 7/2002 | Hugueny et al. |
| 6,427,509 B1 | 8/2002 | Ouchi et al. |
| 6,440,085 B1 | 8/2002 | Krzyzanowski |
| 6,447,511 B1 | 9/2002 | Slater |
| 6,514,197 B1 | 2/2003 | Ouchi et al. |
| 6,514,269 B2 | 2/2003 | Yamamoto |
| 6,551,315 B2 | 4/2003 | Kortenbach et al. |
| 6,554,850 B1 * | 4/2003 | Ouchi ............ A61B 10/06 606/205 |
| 6,561,988 B1 | 5/2003 | Turturro et al. |
| 6,569,085 B2 | 5/2003 | Kortenbach et al. |
| 6,582,451 B1 | 6/2003 | Marucci et al. |
| 6,613,068 B2 | 9/2003 | Ouchi |
| 6,616,662 B2 | 9/2003 | Scholer et al. |
| 6,685,723 B1 | 2/2004 | Ouchi et al. |
| 6,689,122 B2 | 2/2004 | Yamamoto |
| 6,692,445 B2 | 2/2004 | Roberts et al. |
| 6,716,226 B2 | 4/2004 | Sixto, Jr. et al. |
| 6,740,106 B2 | 5/2004 | Kobayashi et al. |
| 6,743,240 B2 | 6/2004 | Smith et al. |
| 6,767,349 B2 | 7/2004 | Ouchi |
| 6,808,491 B2 | 10/2004 | Kortenbach et al. |
| 6,824,548 B2 | 11/2004 | Smith et al. |
| 6,843,794 B2 | 1/2005 | Sixto, Jr. et al. |
| 6,887,240 B1 | 5/2005 | Lands et al. |
| 6,926,676 B2 | 8/2005 | Turturro et al. |
| 6,945,979 B2 | 9/2005 | Kortenbach et al. |
| 6,951,560 B1 | 10/2005 | Kidooka |
| 6,953,430 B2 | 10/2005 | Kidooka |
| 6,964,662 B2 | 11/2005 | Kidooka |
| 6,969,389 B2 | 11/2005 | Kidooka |
| 7,033,315 B2 | 4/2006 | Smith |
| 7,037,276 B2 | 5/2006 | Sayet et al. |
| 7,052,489 B2 | 5/2006 | Griego et al. |
| 7,105,000 B2 | 9/2006 | McBrayer |
| RE39,415 E | 11/2006 | Bales et al. |
| 7,147,638 B2 | 12/2006 | Chapman et al. |
| 7,171,839 B2 | 2/2007 | Krzyzanowski |
| 7,186,261 B2 | 3/2007 | Prestel |
| 7,311,674 B2 | 12/2007 | Gingrich et al. |
| 7,326,209 B2 | 2/2008 | Kidooka |
| 7,341,564 B2 | 3/2008 | Zwiefel et al. |
| 7,354,439 B2 | 4/2008 | Kidooka |
| 7,422,592 B2 | 9/2008 | Morley et al. |
| 7,534,253 B2 | 5/2009 | Endara et al. |
| 7,621,910 B2 | 11/2009 | Sugi |
| 7,736,363 B2 | 6/2010 | Watanabe |
| 7,749,222 B2 | 7/2010 | Lu et al. |
| 7,775,989 B2 | 8/2010 | Nakao |
| 2001/0021860 A1 | 9/2001 | Ouchi |
| 2001/0047124 A1 | 11/2001 | Yamamoto |
| 2001/0051812 A1 | 12/2001 | Ouchi |
| 2002/0010459 A1 | 1/2002 | Whittier et al. |
| 2002/0013595 A1 | 1/2002 | Yamamoto |
| 2002/0043973 A1 | 4/2002 | Amini et al. |
| 2002/0068935 A1 | 6/2002 | Kortenbach |
| 2002/0068945 A1 | 6/2002 | Sixto |
| 2002/0068946 A1 | 6/2002 | Kortenbach |
| 2002/0078967 A1 | 6/2002 | Sixto |
| 2002/0138086 A1 | 9/2002 | Sixto |
| 2002/0165580 A1 | 11/2002 | Zwiefel et al. |
| 2002/0173786 A1 | 11/2002 | Kortenbach |
| 2002/0188220 A1 | 12/2002 | Krzyzanowski |
| 2002/0198537 A1 | 12/2002 | Smith |
| 2002/0198538 A1 | 12/2002 | Kortenbach |
| 2002/0198539 A1 | 12/2002 | Sixto |
| 2002/0198540 A1 | 12/2002 | Smith |
| 2002/0198541 A1 | 12/2002 | Smith et al. |
| 2002/0198549 A1 | 12/2002 | Sixto et al. |
| 2003/0009193 A1 | 1/2003 | Corsaro |
| 2003/0036679 A1 | 2/2003 | Kortenbach et al. |
| 2003/0050574 A1 | 3/2003 | Krueger |
| 2003/0097147 A1 | 5/2003 | Prestel |
| 2003/0144605 A1 | 7/2003 | Burbank |
| 2003/0191464 A1 | 10/2003 | Kidooka |
| 2003/0191478 A1 | 10/2003 | Kortenbach et al. |
| 2003/0195387 A1 | 10/2003 | Kortenbach et al. |
| 2003/0233092 A1 | 12/2003 | Kortenbach et al. |
| 2003/0236549 A1 | 12/2003 | Bonadio et al. |
| 2004/0015165 A1 | 1/2004 | Kidooka |
| 2004/0068291 A1 | 4/2004 | Suzuki |
| 2004/0087979 A1 | 5/2004 | Field et al. |
| 2004/0092967 A1 | 5/2004 | Sancoff et al. |
| 2004/0093019 A1 | 5/2004 | Kothe |
| 2004/0098040 A1 | 5/2004 | Taniguchi et al. |
| 2004/0116948 A1 | 6/2004 | Sixto et al. |
| 2004/0193186 A1 | 9/2004 | Kortenbach et al. |
| 2004/0193214 A1 | 9/2004 | Scheller et al. |
| 2004/0199160 A1 | 10/2004 | Slater |
| 2004/0249411 A1 | 12/2004 | Suzuki |
| 2004/0254592 A1 | 12/2004 | DiCarlo et al. |
| 2004/0260198 A1 | 12/2004 | Rothberg et al. |
| 2004/0260337 A1 | 12/2004 | Freed |
| 2005/0004432 A1 | 1/2005 | Suzuki et al. |
| 2005/0033333 A1 | 2/2005 | Smith et al. |
| 2005/0033354 A1 | 2/2005 | Montalvo et al. |
| 2005/0043758 A1 | 2/2005 | Golden et al. |
| 2005/0049520 A1 | 3/2005 | Nakao |
| 2005/0049616 A1 | 3/2005 | Rivera |
| 2005/0049633 A1 | 3/2005 | Watanabe |
| 2005/0054945 A1 | 3/2005 | Cohen et al. |
| 2005/0090837 A1 | 4/2005 | Sixto et al. |
| 2005/0090838 A1 | 4/2005 | Sixto et al. |
| 2005/0113867 A1 | 5/2005 | Anderhub et al. |
| 2005/0124912 A1 | 6/2005 | Griego et al. |
| 2005/0125010 A1 | 6/2005 | Smith et al. |
| 2005/0131312 A1 | 6/2005 | Endara et al. |
| 2005/0137585 A1 | 6/2005 | Landman et al. |
| 2005/0216029 A1 | 9/2005 | Gingrich et al. |
| 2005/0240218 A1 | 10/2005 | Freed et al. |
| 2005/0261735 A1 | 11/2005 | Shibata |
| 2006/0009711 A1 | 1/2006 | Gingrich et al. |
| 2006/0025780 A1 | 2/2006 | James |
| 2006/0149222 A1 | 7/2006 | Okada |
| 2006/0184198 A1 | 8/2006 | Bales et al. |
| 2006/0206145 A1 | 9/2006 | Griego et al. |
| 2006/0276785 A1 | 12/2006 | Asahara et al. |
| 2007/0055172 A1 | 3/2007 | Ratnakar |
| 2007/0078458 A1 | 4/2007 | Dumbauld et al. |
| 2007/0149971 A1 | 6/2007 | Nishimura |
| 2007/0198011 A1 | 8/2007 | Sugita |
| 2007/0244507 A1 | 10/2007 | Szweda et al. |

(56) References Cited

U.S. PATENT DOCUMENTS

| | | |
|---|---|---|
| 2007/0244508 A1 | 10/2007 | Weizman et al. |
| 2007/0244509 A1 | 10/2007 | Weizman et al. |
| 2007/0244510 A1 | 10/2007 | Weizman et al. |
| 2007/0244511 A1 | 10/2007 | Weizman et al. |
| 2007/0244512 A1 | 10/2007 | Measamer |
| 2007/0244513 A1 | 10/2007 | Weizman et al. |
| 2007/0244514 A1 | 10/2007 | Weizman et al. |
| 2008/0064982 A1 | 3/2008 | Nowlin et al. |
| 2008/0125769 A1 | 5/2008 | Suzuki et al. |
| 2008/0171908 A1 | 7/2008 | Okada et al. |
| 2008/0194910 A1 | 8/2008 | Miyamoto et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0131932 A1 | 5/2009 | Vakharia et al. |
| 2009/0131933 A1 | 5/2009 | Ghabrial et al. |
| 2009/0216078 A1 | 8/2009 | Iwanaga et al. |
| 2009/0264918 A1 | 10/2009 | Endara et al. |
| 2009/0287112 A1 | 11/2009 | Freeman |
| 2010/0106068 A1 | 4/2010 | Karpiel et al. |

FOREIGN PATENT DOCUMENTS

| | | |
|---|---|---|
| DE | 85 32 644.5 U1 | 5/1986 |
| DE | 87 12 328.2 U1 | 3/1988 |
| DE | 88 14 560.3 U1 | 3/1989 |
| DE | 39 20 706 A1 | 1/1991 |
| DE | 40 06 673 A1 | 9/1991 |
| DE | 40 12 882 C2 | 3/1992 |
| DE | 92 11 834.8 U1 | 4/1993 |
| DE | 296 14 931 U1 | 3/1997 |
| DE | 199 04 723 A1 | 8/1999 |
| DE | 199 48 387 A1 | 5/2000 |
| DE | 100 18 674 A1 | 11/2000 |
| DE | 100 48 369 A1 | 4/2001 |
| DE | 100 51 651 A1 | 4/2001 |
| DE | 100 56 946 A1 | 5/2001 |
| DE | 100 43 163 A1 | 6/2001 |
| DE | 101 10 929 A1 | 9/2001 |
| DE | 101 28 553 A1 | 1/2002 |
| DE | 101 23 848 A1 | 3/2002 |
| DE | 101 56 313 A1 | 6/2003 |
| DE | 103 16 134 A1 | 10/2003 |
| DE | 100 48 369 C2 | 12/2003 |
| DE | 103 32 613 A1 | 2/2004 |
| DE | 10 2004 031 703 A1 | 3/2005 |
| DE | 600 09 733 T2 | 3/2005 |
| DE | 100 18 674 B4 | 6/2005 |
| DE | 103 53 006 A1 | 6/2005 |
| DE | 697 31 096 T2 | 10/2005 |
| DE | 10 2005 023 852 A1 | 12/2005 |
| DE | 100 51 652 B4 | 2/2006 |
| DE | 103 53 006 B4 | 2/2006 |
| EP | 0 207 829 A1 | 1/1987 |
| EP | 0 207 830 A1 | 1/1987 |
| EP | 317 526 | 5/1989 |
| EP | 0 380 874 A1 | 8/1990 |
| EP | 0 507 620 B1 | 10/1992 |
| EP | 0 593 929 A1 | 9/1993 |
| EP | 0 573 817 A1 | 12/1993 |
| EP | 0 367 818 B1 | 3/1994 |
| EP | 0 585 921 A1 | 3/1994 |
| EP | 0 598 607 A2 | 5/1994 |
| EP | 0 491 890 B1 | 2/1996 |
| EP | 0 592 243 B1 | 4/1997 |
| EP | 0 621 009 B1 | 7/1997 |
| EP | 0 573 817 B1 | 7/1998 |
| EP | 1 312 313 A1 | 5/2003 |
| EP | 1 371 332 A1 | 12/2003 |
| EP | 1 001 706 B1 | 3/2004 |
| EP | 1 221 896 B1 | 4/2004 |
| EP | 1 462 063 A1 | 9/2004 |
| EP | 0 921 758 B1 | 10/2004 |
| EP | 1 472 982 A2 | 11/2004 |
| EP | 1 161 183 B1 | 10/2005 |
| EP | 1 607 049 A1 | 12/2005 |
| EP | 1 607 050 A1 | 12/2005 |
| EP | 1 607 055 A1 | 12/2005 |
| EP | 1 872 730 | 1/2008 |
| EP | 1 875 872 | 1/2008 |
| FR | 2 751 199 A1 | 1/1998 |
| FR | 2 864 888 A1 | 7/2005 |
| JP | 2-1251 | 1/1990 |
| JP | 06-217987 A | 8/1993 |
| JP | 05-309097 A | 11/1993 |
| JP | 06-189966 A | 7/1994 |
| JP | 06-197906 A | 7/1994 |
| JP | 07-313514 A | 12/1995 |
| JP | 08-206120 A | 8/1996 |
| JP | 09-075356 A | 3/1997 |
| JP | 09-098978 A | 4/1997 |
| JP | 09-507150 | 7/1997 |
| JP | 09-508561 T2 | 9/1997 |
| JP | 10-024045 A | 1/1998 |
| JP | 10-028692 A | 2/1998 |
| JP | 10-118015 A | 5/1998 |
| JP | 10-118076 A | 5/1998 |
| JP | 10-118091 A | 5/1998 |
| JP | 10-137251 A | 5/1998 |
| JP | 10-165408 A | 6/1998 |
| JP | 10-506035 | 6/1998 |
| JP | 09-276285 A | 10/1998 |
| JP | 11-019085 A | 1/1999 |
| JP | 11-19086 | 1/1999 |
| JP | 11-19087 | 1/1999 |
| JP | 11-033032 A | 2/1999 |
| JP | 11-047135 A | 2/1999 |
| JP | 11-076244 A | 3/1999 |
| JP | 11-155877 | 6/1999 |
| JP | 11-178829 | 7/1999 |
| JP | 11-509132 T2 | 8/1999 |
| JP | 11-509459 T2 | 8/1999 |
| JP | 2000-175920 A | 6/2000 |
| JP | 2000-175928 A | 6/2000 |
| JP | 2000-189429 A | 7/2000 |
| JP | 2000-189430 A | 7/2000 |
| JP | 2000-189431 | 7/2000 |
| JP | 2000-189432 A | 7/2000 |
| JP | 2000-189433 A | 7/2000 |
| JP | 2000-189434 A | 7/2000 |
| JP | 2000-189435 A | 7/2000 |
| JP | 2000-271128 | 10/2000 |
| JP | 2000-296131 A | 10/2000 |
| JP | 3150157 B2 | 1/2001 |
| JP | 2001-029349 A | 2/2001 |
| JP | 2001-070239 A | 3/2001 |
| JP | 2001-070308 A | 3/2001 |
| JP | 2001-070309 A | 3/2001 |
| JP | 2001-079009 | 3/2001 |
| JP | 2001-095807 A | 4/2001 |
| JP | 2001-095808 A | 4/2001 |
| JP | 2001-104318 A | 4/2001 |
| JP | 2001-112763 A | 4/2001 |
| JP | 2001-112764 A | 4/2001 |
| JP | 2001-112765 A | 4/2001 |
| JP | 2001-137998 A | 5/2001 |
| JP | 3190029 B2 | 5/2001 |
| JP | 2001-190556 A | 7/2001 |
| JP | 3220164 B2 | 8/2001 |
| JP | 3220165 B2 | 8/2001 |
| JP | 2001-245891 A | 9/2001 |
| JP | 2001-321385 A | 11/2001 |
| JP | 2001-321386 A | 11/2001 |
| JP | 2001-340347 A | 12/2001 |
| JP | 2002-017734 A | 1/2002 |
| JP | 2002-034989 A | 2/2002 |
| JP | 2002-045363 A | 2/2002 |
| JP | 2002-065598 A | 3/2002 |
| JP | 2002-119514 A | 4/2002 |

(56) References Cited

FOREIGN PATENT DOCUMENTS

| | | |
|---|---|---|
| JP | 2003-093393 A | 4/2002 |
| JP | 2002-153475 A | 5/2002 |
| JP | 2002-191605 A | 7/2002 |
| JP | 2002-191606 A | 7/2002 |
| JP | 2002-282265 A | 10/2002 |
| JP | 2002-330973 A | 11/2002 |
| JP | 2003-126103 A | 5/2003 |
| JP | 2003-235851 A | 8/2003 |
| JP | 2003-299669 | 10/2003 |
| JP | 2003-310635 | 11/2003 |
| JP | 2004-000424 A | 1/2004 |
| JP | 2004-049330 A | 2/2004 |
| JP | 2004-97615 | 4/2004 |
| JP | 3569469 B2 | 6/2004 |
| JP | 2004-229976 | 8/2004 |
| JP | 2005-021346 A | 1/2005 |
| JP | 2005-058344 | 3/2005 |
| JP | 2005-152463 A | 6/2005 |
| JP | 2005-193061 | 7/2005 |
| JP | 2005-224426 A | 8/2005 |
| JP | 2005-237431 | 9/2005 |
| JP | 2006-296578 | 11/2006 |
| JP | 2006-296781 | 11/2006 |
| JP | 2006-334267 | 12/2006 |
| JP | 2006-334348 | 12/2006 |
| JP | 2007-260248 | 10/2007 |
| JP | 2007-330436 | 12/2007 |
| JP | 2009-153535 | 7/2009 |
| JP | 2009-297503 | 12/2009 |
| WO | WO 89/10093 A1 | 11/1989 |
| WO | WO 90/01297 A1 | 2/1990 |
| WO | WO 91/16856 A1 | 11/1991 |
| WO | WO 93/20754 | 10/1993 |
| WO | WO 94/17741 | 8/1994 |
| WO | WO 96/09004 | 3/1996 |
| WO | WO 96/09004 A1 | 3/1996 |
| WO | WO 96/19144 A1 | 6/1996 |
| WO | WO 97/11643 | 4/1997 |
| WO | WO 97/12558 A1 | 4/1997 |
| WO | WO 97/41776 A1 | 11/1997 |
| WO | WO 97/41777 A1 | 11/1997 |
| WO | WO 98/03116 A1 | 1/1998 |
| WO | WO 98/06336 A1 | 2/1998 |
| WO | WO 98/26723 A1 | 6/1998 |
| WO | WO 99/07287 A1 | 2/1999 |
| WO | WO 00/01304 A1 | 1/2000 |
| WO | WO 00/07502 A1 | 2/2000 |
| WO | WO 00/54658 A1 | 9/2000 |
| WO | WO 01/24706 A1 | 4/2001 |
| WO | WO 01/28427 A1 | 4/2001 |
| WO | WO 03/000115 A2 | 1/2003 |
| WO | WO 03/024300 A1 | 3/2003 |
| WO | WO 03/028557 A1 | 4/2003 |
| WO | WO 03/099139 A1 | 12/2003 |
| WO | WO 2005/009255 A1 | 2/2005 |
| WO | WO 2005/025432 A1 | 3/2005 |
| WO | WO 2005/041789 A1 | 5/2005 |
| WO | WO 2005/063127 A1 | 7/2005 |
| WO | WO 2005/072663 A1 | 8/2005 |
| WO | WO 2006/114952 | 11/2006 |
| WO | WO 2006/114989 | 11/2006 |

* cited by examiner

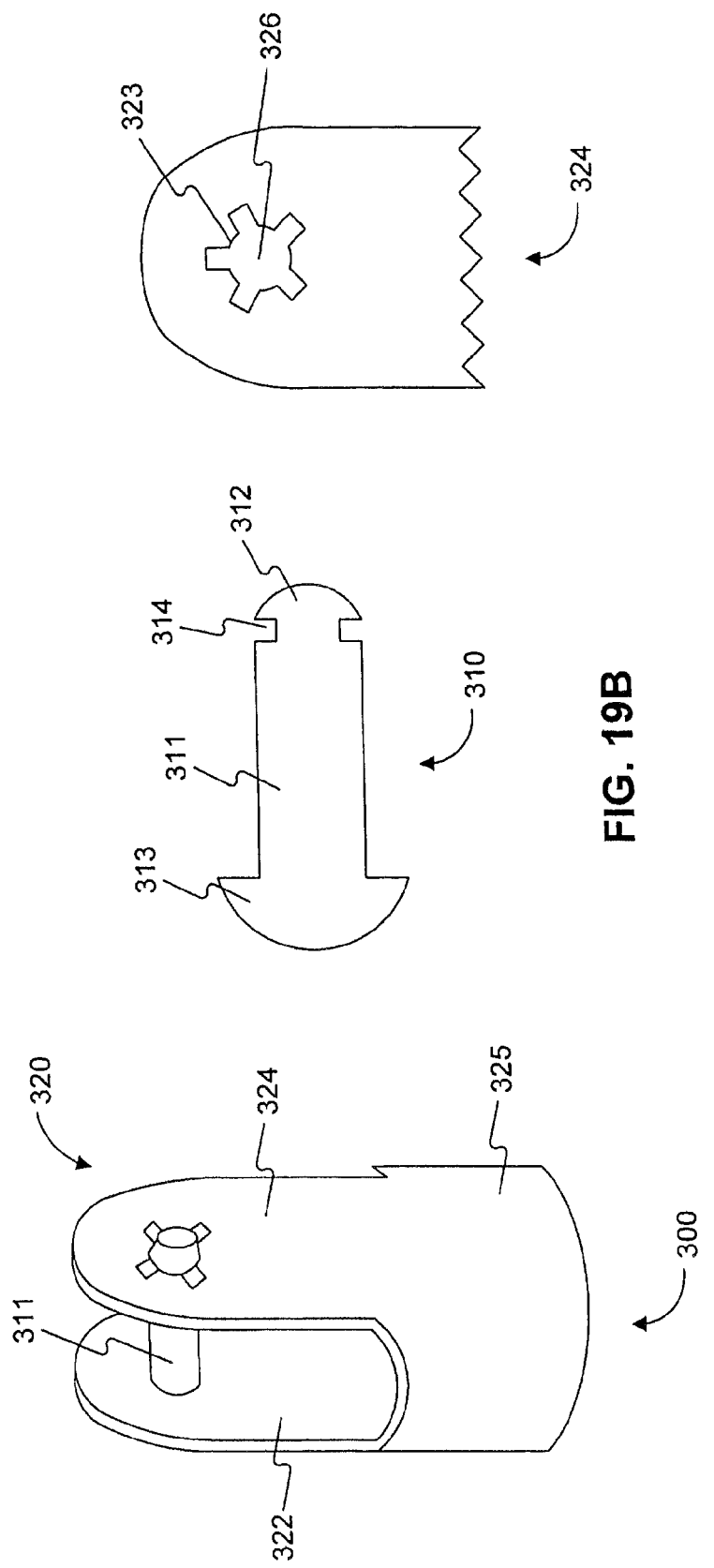

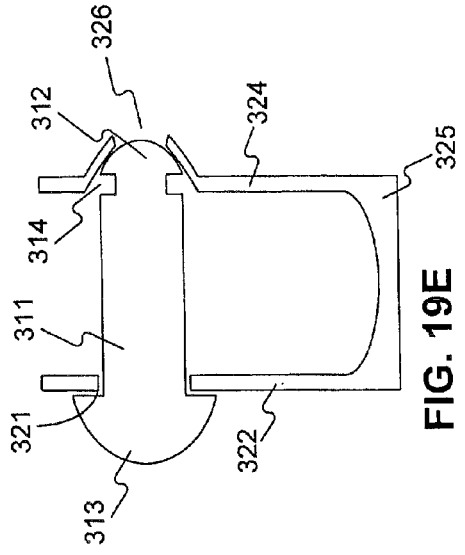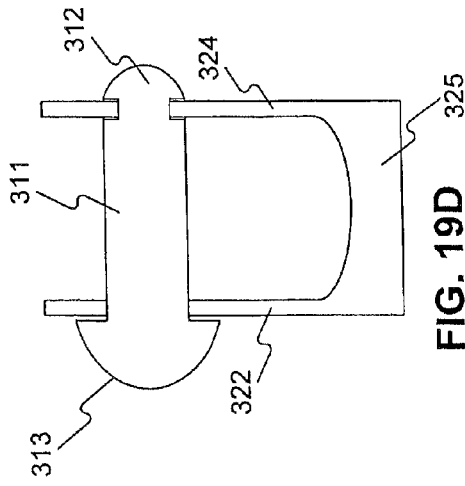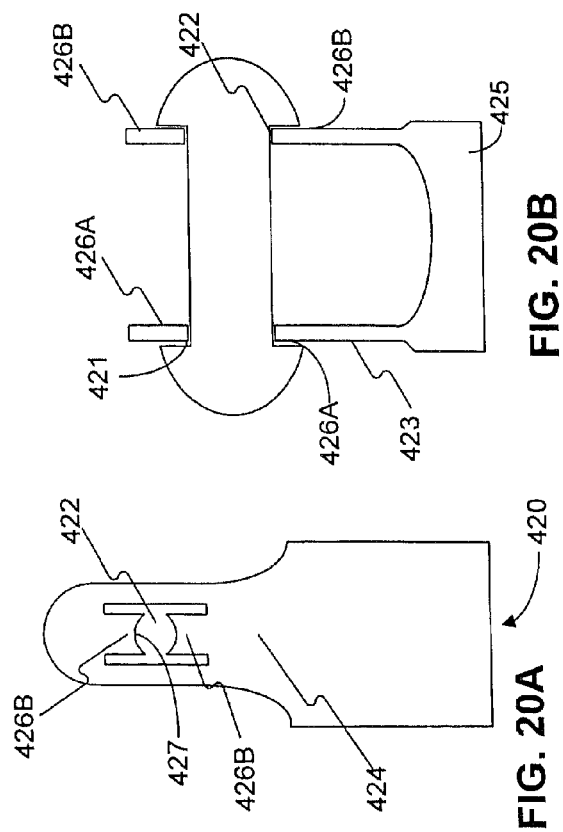

ND OSCOPIC INSTRUMENTS AND
METHODS OF MANUFACTURE

ENDOSCOPIC INSTRUMENTS AND METHODS OF MANUFACTURE

CROSS-REFERENCE TO RELATED APPLICATION

This application is a continuation of U.S. application Ser. No. 10/845,108, filed May 14, 2004, which is a continuation-in-part of U.S. patent application Ser. No. 10/778,226 filed Feb. 17, 2004, which claims the benefit under 35 U.S.C. §§119, 120 of U.S. Provisional Patent Application No. 60/479,145 filed Jun. 18, 2003, the entirety of all of which are incorporated herein by references.

DESCRIPTION OF THE INVENTION

Field of the Invention

Embodiments of the invention include a medical device with one or more of a variety of features. More particularly, embodiments of the invention relate to endoscopic devices that include one or more features that improve the use of the device. Examples of such features include chamfered edges and corners on, for example, the end effectors, a surface with a controlled finish also on, for example, the end effectors, a jaw with teeth and/or a tang having various configurations, a handle having soft-grip features; and/or an elongate member with varied rigidity. Other examples of such features include a folded portion on, for example, the end effectors and/or a snap-fit clevis assembly.

Background of the Invention

Various medical instruments may be used in connection with an endoscope for performing a number of operations at a site deep within a patient's body cavity. One such instrument, a biopsy forceps device, samples tissue from a body cavity with minimal intervention and discomfort to patients. Typically, a biopsy forceps device, like other endoscopic instruments, has a long flexible tubular member for insertion into a lumen of an endoscope. The tubular member is sufficiently long and flexible to follow a long, winding path of the body cavity. An end effector assembly, such as a biopsy forceps assembly, is attached at a distal end of the tubular member, and a handle is attached at a proximal end of the tubular member. The handle may have an elongate portion and a spool portion disposed around the elongate portion. The spool portion may be configured to move longitudinally relative to the elongate portion. An elongate mechanism, such as one or more pull wires, extends through the tubular member to connect the end effector assembly and a portion of the handle, such as the spool portion. Longitudinal movement of the spool portion relative to the elongate portion of the handle causes the elongate mechanism to move longitudinally in the tubular member, which in turn causes the actuation of the end effector assembly.

In methods of using the biopsy forceps device, an endoscope is placed in a patient's body cavity adjacent a tissue site from which the acquisition of a tissue sample is desired. The biopsy forceps device is then advanced to the tissue site, via a working channel of the endoscope. Once the biopsy forceps device is next to the portion of the tissue from which the acquisition of a tissue sample is desired, the spool portion is moved relative to the elongate portion so as to move pull wires. The movement of the pull wires causes the jaws of the biopsy forceps assembly to open. The open jaws are then advanced to the tissue site, and the spool portion is again moved relative to the elongate portion so as to move the pull wires such that the jaws close. The closing of the jaws causes a tissue sample to be captured in the end effector assembly. The biopsy forceps device is then removed from the body cavity via the working channel of the endoscope.

SUMMARY OF THE INVENTION

In accordance with the invention, an embodiment of the invention includes a medical device including a handle, an end effector assembly, and a member connecting the handle to the end effector assembly. The end effector assembly includes an end effector having non-sharp edges and corners.

Another embodiment of the invention includes a medical device including a handle, an end effector assembly, and a member connecting the handle to the end effector assembly. Portions of the end, effector assembly have a roughened surface.

Yet another embodiment of the invention includes a medical device including a handle, an end effector assembly, and a member connecting the handle to the end effector assembly. The end effector assembly includes opposing jaw portions each including a plurality of teeth. Each of the teeth includes a crest, a root, and an intermediate portion between the crest and the root. The intermediate portions of opposing jaw portions are configured to contact each other when the opposing jaw portions are brought together and the root has a recessed portion configured to accommodate a sharp, pointed tip of the crest.

Still another embodiment of the invention includes a medical device including a handle, an end effector assembly, and a member connecting the handle to the end effector assembly. The end effector assembly includes at least one end effector having a tang defining a mounting hole configured to receive one of a wire and an axle and the tang includes a portion disposed around the mounting hole that, has a thickness greater than a thickness of other portions of the tang.

A further embodiment of the invention includes a medical device including a handle, an end effector assembly, and a member connecting the handle to the end effector assembly. The end effector assembly includes at least one biopsy jaw having a tissue receiving portion that defines at least one hole configured so as to substantially prevent contact between an edge of the hole and a tube-like member in which the end effector assembly is configured to extend through.

A yet further embodiment of the invention includes a medical device including a soft-grip handle, an end effector assembly, and a member connecting the handle to the end effector assembly.

A still further embodiment of the invention includes a medical device, including a handle, an end effector assembly, and an elongate, flexible member connecting the handle to the end effector assembly. A proximal portion of a distal third of the elongate member is more flexible than adjacent portions of the elongate member.

Another embodiment of the invention includes a medical device including a handle, an end effector assembly, and an elongate, flexible member connecting the handle to the end effector assembly. The end effector assembly includes a pair of opposing biopsy jaws each having a tissue receiving portion having a roughened surface and defining a hole, the hole configured so as to substantially prevent contact between an edge of the hole and a tube-like member in which the end effector assembly is configured to extend through. Each biopsy jaw further includes a tang defining a mounting hole configured to receive one of a wire and an axle, the tang including a portion disposed around the mounting hole that has a thickness greater than a thickness of other portions of the tang. Each biopsy jaw further includes a plurality of teeth, each of the teeth including a crest, a root, and an intermediate portion between the crest and the root. The intermediate portions of opposing biopsy jaws are configured to contact each other when the biopsy jaws are brought together, and the root has a recessed portion configured to accommodate a sharp, pointed tip of the crest.

Various embodiments of the invention may have any or all of the following features: wherein the end effector defines a hole having a non-sharp edge. The end effector may include a jaw extending from an arm, and wherein all edges of the jaw other than a cutting edge of the jaw are non-sharp. The non-sharp edges and corners may be beveled. Portions of the end effector assembly may have a rougher surface than other portions of the end effector assembly. The end effector assembly may include a biopsy forceps jaw having a roughened surface. The roughened surface of the biopsy forceps jaws may be an outer surface of the biopsy forceps jaw. The roughened surface of the biopsy forceps jaws may be an inner surface of the biopsy forceps jaw. The roughened surface may be formed by one of grit blasting, media tumbling, plating, sputtering, photo-etching, acid-etching, and plasma coating. The root may be at least a partial, substantially circular cutout. A center of the cutout may be displaced vertically relative to adjacent intermediate portions. A center of the cutout may be displaced horizontally relative to a center of adjacent intermediate portions. The root may be a U-shaped groove. A center of the U-shaped groove may be displaced vertically relative to adjacent intermediate portions. A center of the U-shaped groove may be displaced horizontally relative to a center of adjacent intermediate portions. A gap may be between the tip and the root of opposing teeth when the opposing jaw portions are brought together. A wire having a first wire portion may be substantially contacting one side of the tang and a second wire portion substantially contacting another side of the tang. The at least one end effector may include two end effectors. The wire may be bent on both sides of the mounting hole. A section of the tang defining a through hole may be folded so that the through hole is substantially aligned with the mounting hole. The at least one end effector may define a second mounting hole configured to receive the other of the wire and the axle, and wherein the tang includes a second portion around the second mounting hole that has a thickness greater than the thickness of other portions of the tang. The hole may be disposed off a centerline of the biopsy jaw. The at least one biopsy jaw may include two biopsy jaws. The at least one hole may include a plurality of holes. The handle may have a ring portion connected to an elongate portion, and a spool portion disposed around the elongate portion, and wherein the ring portion and the spool portion have a soft-grip configuration. The handle may have a plurality of finger rings, and wherein the finger rings have a soft-grip configuration. The soft-grip handle may include a low durometer material. The soft-grip handle may include at least one of santoprene and urethane.

A further embodiment of the invention includes an end effector assembly for a medical instrument. The end effector assembly includes an end effector having a tang defining a pivot hole. An edge of the tang proximal to the pivot hole extends within an outer periphery of the tang.

Still another embodiment of the invention includes a medical device. The medical device includes a handle, an end effector assembly, and a member connecting the handle to the end effector assembly. The end effector assembly includes an end effector having a tang defining a pivot hole. An edge of the tang proximal to the pivot hole extends within an outer periphery of the tang.

Various embodiments of the invention may have any or all of the following features: the tang may be configured to substantially prevent contact between the edge and a channel in which the end effector assembly is configured to extend through, as the end effector pivots about the pivot hole; a section of the tang at the outer periphery adjacent the edge may have a smooth surface; a first tang portion extending from the outer periphery to the edge may form less than a 90 degree angle to a second tang portion extending from the outer periphery and defining the pivot hole; the first tang portion and the second tang portion may form an approximately zero degree angle; the first tang portion and the second tang portion may be substantially parallel; a section of the tang between the outer periphery adjacent the edge and the edge may be curved; the edge may be substantially sharp.

A still further embodiment of the invention includes a clevis assembly for a medical instrument. The clevis assembly includes a clevis having a base and a first arm and a second arm extending from the base and an axle extending between the first arm and the second arm. The axle defines a groove in which a portion of the first arm is disposed.

Yet another embodiment of the invention includes a clevis assembly for a medical instrument. The clevis assembly includes a clevis having a base and a first arm and a second arm extending from the base and an axle extending between the first arm and the second arm. A portion of the first arm is configured to deflect from an original configuration and return to the original configuration as the axle is placed through the first arm.

A yet further embodiment of the invention includes a medical instrument. The medical instrument includes a handle portion, an end effector assembly, and an elongate member connecting the handle portion to the end effector assembly. The end effector assembly includes a clevis having a base and a first arm and a second arm extending from the base and an axle extending between the first arm and the second arm. The axle defines a groove in which a portion of the first arm is disposed.

Another embodiment of the invention includes a medical instrument. The medical instrument includes a handle portion, an end effector assembly, and an elongate member connecting the handle portion to the end effector assembly. The end effector assembly includes a clevis having a base and a first arm and a second arm extending from the base and an axle extending between the first arm and the second arm. A portion of the first arm is configured to deflect from an original configuration and return to the original configuration as the axle is placed through the first arm.

Various embodiments of the invention may have any or all of the following features: the portion may be configured to deflect from an original configuration as the axle is placed through the first arm; the portion may be configured to substantially return to the original configuration for disposition in the groove; the portion may include a plurality of protrusions defining a hole in the first arm; the protrusions may deflect; the second arm may define a hole, and a portion of the axle at an end opposite the groove may be configured to prevent passage of the portion of the axle through the hole; an end of the axle may have a larger circumference than a central portion of the axle; and the axle may include end portions having cross-sectional sizes larger than a hole defined by the portion of the first arm.

A further embodiment of the invention includes a method of manufacturing an end effector assembly of a medical instrument. The method includes providing a clevis having a base and a first arm and a second arm extending from the base, providing an axle, placing an axle through the second arm, placing the axle through the first arm so as to deflect a portion of the first arm, and returning the portion of the first arm to its original configuration.

Various embodiments of the invention may have any or all of the following features: the portion of the first arm in a groove on the axle; providing an end effector; placing the axle through a portion of the end effector.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 19A is a perspective view of a clevis assembly according to yet another embodiment of the present invention.

FIG. 19B is a side view of an axle of the clevis assembly of FIG. 19A.

FIG. 19C is a partial side view of a portion of the clevis assembly of FIG. 19A.

FIG. 19D is a schematic view of the clevis assembly of FIG. 19A.

FIG. 19E is a schematic view of the clevis assembly of FIG. 19A, with the axle being inserted into the clevis.

FIG. 20A is a side view of a clevis according to still another embodiment of the present invention.

FIG. 20B is a schematic view of an axle in the clevis of FIG. 20A.

FIG. 20C is a schematic view of the axle and clevis of FIG. 20A.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Figure 1:
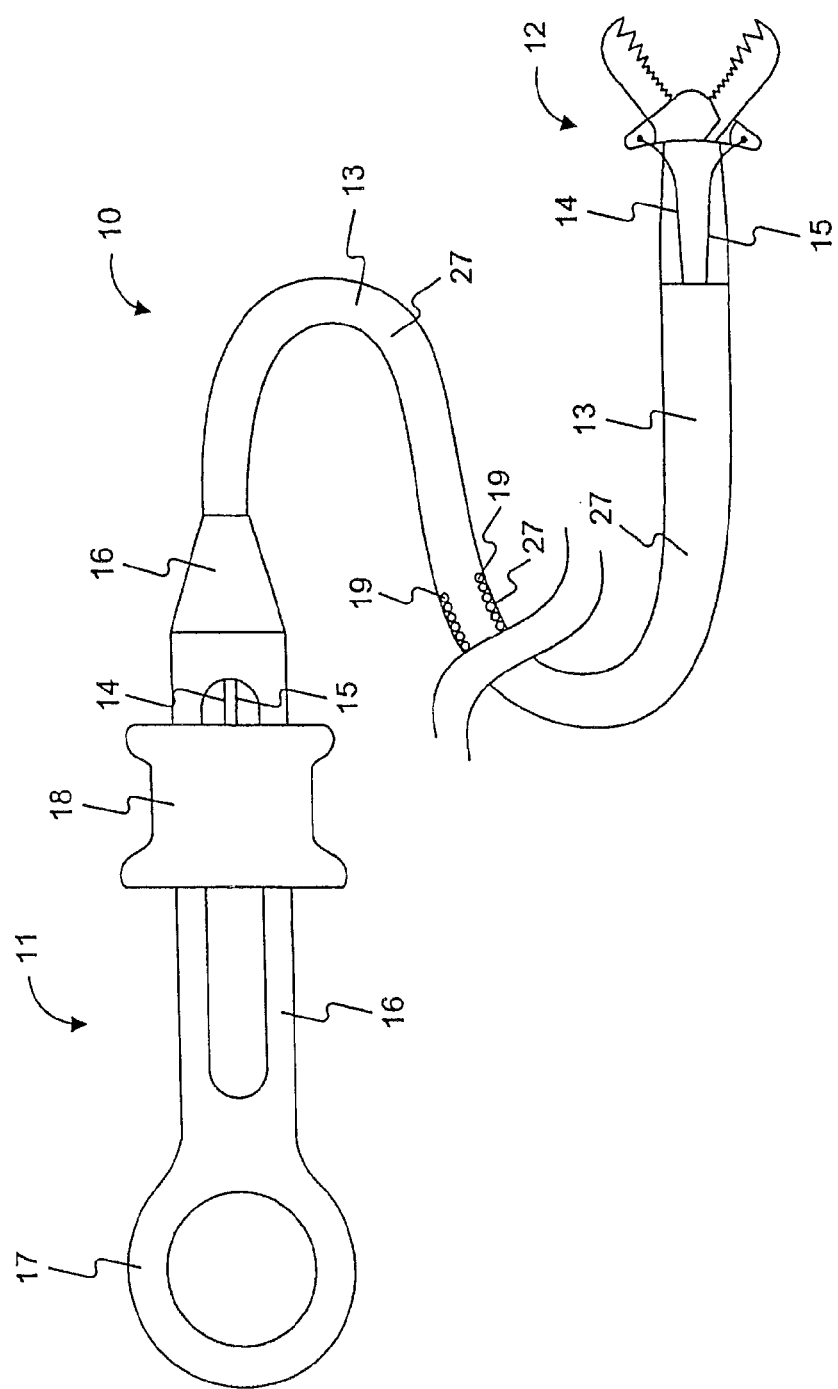
FIG. 1 is a perspective view of an endoscopic instrument suitable for use in connection with embodiments of the present invention.

An exemplary embodiment of a medical device is depicted in FIG. 1. The medical device is an endoscopic instrument 10 that includes a handle portion 11 and an end effector assembly 12 connected to each other by a flexible elongate member 13. Control wires 14, 15 extend between the handle portion 11 and the end effector assembly 12 via a lumen in the flexible elongate member 13. The handle portion 11 includes an elongate portion 16 connected at its proximal end to a ring portion 17 and a spool portion 18 slidably disposed around the elongate portion 16. The elongate member 13 may having a coiled portion 19 (partially shown in FIG. 1) covered by an outer jacket or a sheath 27. However, the elongate member 13 may not have a coiled portion 19, and instead may include a single layer tubular member. The end effector assembly 12 may be any type of assembly, for example, a biopsy forceps jaw as depicted in FIG. 1. The control wires 14, 15 may be connected at their distal ends to opposing portions of the end effector assembly 12, and at their proximal ends to spool portion 18. Longitudinal movement of the spool portion 18 relative to the elongate portion 16 causes the actuation of the end effector assembly 12 via the control wires 14, 15. Portions of the control wires 14, 15 disposed in the handle 16 may be contained within a tube also disposed in the handle 16. The tube may provide the compressive strength that may be needed to actuate the end effector assembly 12.

Figure 2:
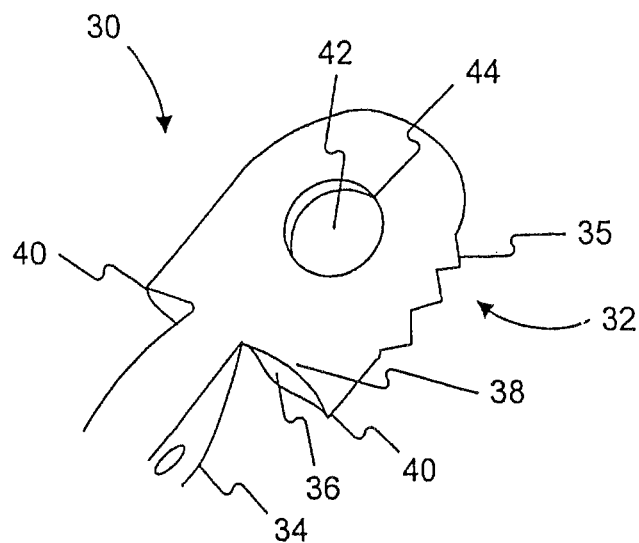
FIG. 2 is a perspective view of a jaw portion of an endoscopic instrument.

A current biopsy forceps jaw 30, such as that shown in FIG. 2, includes a jaw 32 extending from an arm 34. Jaw 32 includes a sharp edge or teeth 35 at its cutting edge. Teeth 35 may mate with another biopsy forceps jaw, of like or similar construction, of an endoscopic forceps instrument to obtain a biopsy sample. Jaw 32 also includes flat surfaces on various parts of jaw 32. For example, the back or proximal-most surface 36 of jaw 32 and certain surfaces intersecting with surface 36 may be flat. The intersection of those surfaces will result in sharp corners and edges, such as edges 38 and corners 40. Jaw 32 also defines a fenestration hole 42 that may include a sharp edge 44. Many current biopsy forceps jaws have such a construction because they are cast from a molded plastic pattern. Certain efficiencies in the manufacture of injection molds lead to flat, intersecting planes and sharp edges and corners of the resultant jaws. These sharp edges and corners, however, may get caught within an endoscope working channel upon entry or exit of a biopsy forceps device through that channel or at the distal end of the endoscope upon re-entry of the forceps after use.

Figure 3:
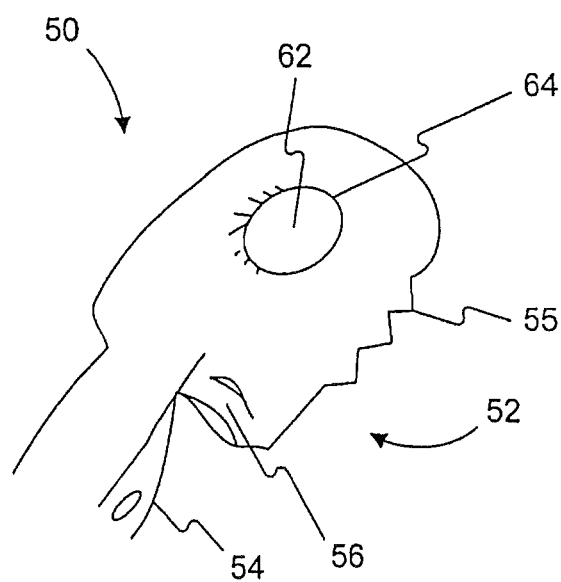
FIG. 3 is a perspective view of a jaw portion of an endoscopic instrument according to an embodiment of the present invention.

Embodiments of the invention include a medical device or portions of the medical device with chamfered corners and/or edges. FIG. 3 shows a biopsy forceps jaw 50 according to an exemplary embodiment of the present invention. The biopsy forceps jaw 50 includes a jaw 52 extending from an arm 54. Like jaw 32 of FIG. 2, jaw 52 includes a sharp edge or teeth 55 at a cutting edge. Unlike jaw 32, however, certain surfaces of jaw 52 are not substantially flat and, instead, are rounded at least near the edges of those surfaces. The corners and edges of various intersecting surfaces are therefore chamfered, beveled, rounded, and/or radiused off and not sharp. For example, the back or proximal-most surface 56 of jaw 52 and certain surfaces intersecting with surface 56 are rounded at least near the edges of those surfaces so that there are no, or fewer, sharp edges or corners associated with jaw 32 (other than the sharp cutting edge having teeth). Jaw 52 also defines a fenestration hole 62 that may include an edge 64 that is rounded, chamfered, beveled, and/or radiused, off so that there is not a sharp edge. The resulting jaw will have no, or fewer, sharp edges or corners to catch within an endoscope working channel upon entry or exit of a biopsy forceps device through that channel or at the distal end of the endoscope upon re-entry of the forceps after use. Less interference with at least the distal section of the endoscope results.

Providing a medical device, or portions thereof, with non-sharp edges and corners may apply to other types of end effectors or other parts of endoscopic or non-endoscopic instruments, including, but not limited to graspers, scissors, forceps, or other laproscopic, endoscopic, or other devices. For example, the medical device may have a sharp cutting edge that is a radial edge (i.e., a straight cutting edge with no teeth). Other edges, corners, and surface intersections, aside from those mentioned above, may be rounded, chamfered, beveled, and/or radiused off as desired to minimize the effects associated with sharp regions as the device is being used. For example, other portions of the end effector assembly, including tang portions, clevis portions, and/or axle portions may include rounded, chamfered, beveled, and/or radiused off edges and corners.

Figure 5:
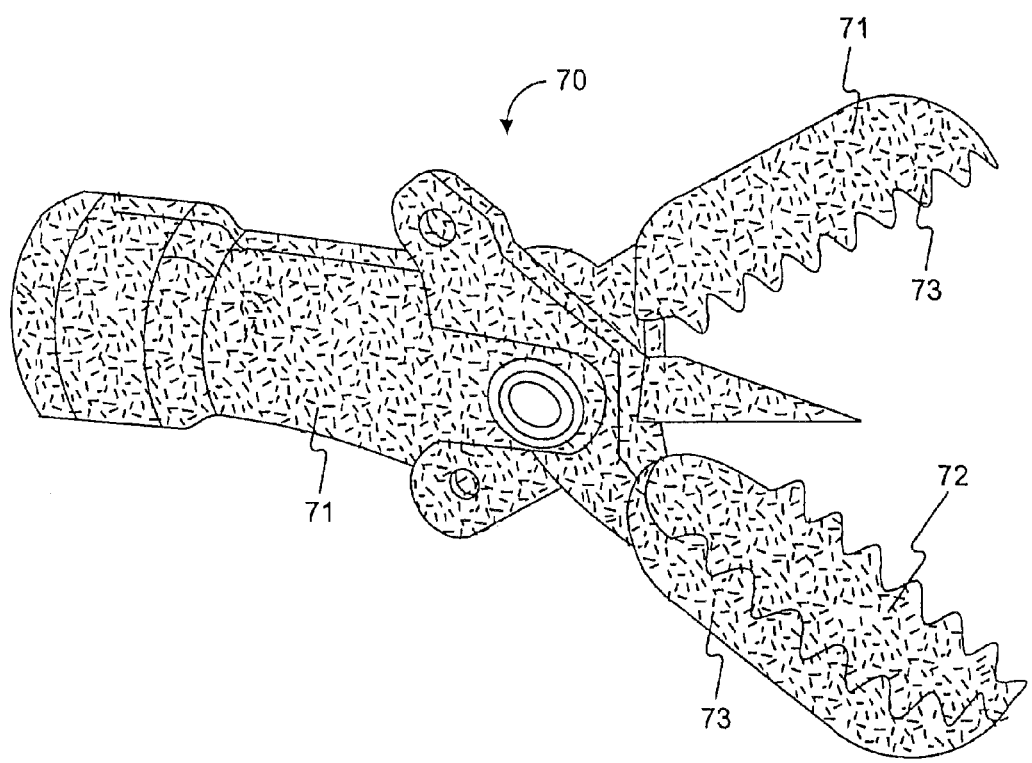
FIG. 5 is a perspective view of a jaw assembly of an endoscopic instrument according to an embodiment of the present invention.

Embodiments of the invention include a medical device or portions of the medical device having a controlled surface finish, including a roughened surface finish. FIG. 5 shows the inner surface 72 and outer surface 71 of a biopsy forceps jaw assembly 70 having a rough surface finish. While FIG. 5 shows a biopsy forceps jaw assembly 70 having all parts with a roughened surface, less than all of the parts of the jaw assembly 70 may include a roughened or textured surface. For example, to attain many of the advantaged described herein, it may be desirable for only the jaws 73, or portions of the jaws 73 such as the outer surface 71, to have a roughened or otherwise textured surface.

Tissues are less prone to sticking to surfaces of jaws having a rough finish than surfaces of jaws having a smooth finish. For example, tissue samples cut with the roughened jaws 73 may be less prone to sticking to the surfaces 71, 72 of the jaws 73. By lessening the smoothness of the inner surface 72 of the jaws 73, the tissue sample may be more easily removed from the jaws 73, for example, when the tissue sample is discharged into an external container.

One potential advantage of having a controlled roughness on the surface of the jaws is that by reducing the amount of sticking, surface contact, and/or seal between the tissue samples and the biopsy jaws, the amount of time spent in a biopsy tissue acquisition procedure is reduced. For example, the amount of time spent trying to release the surface contact between the tissue samples and the surfaces of the jaws, during multiple sample acquisition and/or removing the samples from the jaws into an external specimen container, is reduced. This may permit faster turnaround when a single bite biopsy forceps assembly needs to be removed from an endoscope, the tissue sample retrieved from the jaw, and the assembly reinserted into the endoscope to obtain a subsequent sample.

Another potential advantage for having a rough finish on the surface of the endoscopic instrument is that it reduces surface contact between jaws and/or prevents surfaces of the jaws from sealing and/or sticking to each other. Smooth surfaces may sometimes stick together and form a seal, particularly if a fluid is placed between the surfaces. Having a rough finish on the surface of the jaws reduces the force with which that particular surface of the jaws will stick to either each other or another surface. For example, the surfaces of the teeth of opposing jaws may be less prone to sticking to each other when brought together.

Yet another potential advantage for controlling the surface finish of an endoscopic instrument is that it may provide a more consistent feel and/or performance to the user. For example, the entire endoscopic instrument may have a particular finish, or portions of the endoscopic instrument, such as the end effectors, may have different finishes.

A further potential advantage for controlling the surface finish of an endoscopic instrument is that, for example, when an optimum level of roughness is provided to the surface of the jaw assembly, tissue is more readily grasped and retained in the jaws, for example, so that multiple samples may be collected with a single bite forceps. The controlled surface texture may allow a user to obtain subsequent tissue samples with the prior sample(s) remaining within the jaws. A particular texture of the jaws may allow the tissue sample to be retained within the open jaws while the user acquires a second sample.

A still further potential advantage for controlling the surface finish of an endoscopic instrument is that, for example, when an optimum level of roughness is provided to the surface of the jaw assembly, the roughened surface may assist in both retaining and removing the sample. Such assistance may be dependent on the presence or absence of an external force. For example, when there is no external force exerted on the sample, the roughened surface may assist in the retention of the sample. In another example, when an external force is applied to the sample, the roughened surface may assist in the removal of the sample.

The roughness of the surfaces 71, 72 of the jaw assembly 70 may be created and/or adjusted, for example, by controlling the casting of the jaws 73 and/or subsequent processing of the jaw assembly 70. Subsequent processing may including grit blasting, media tumbling, and/or any other suitable surface finishing technique. The surfaces 71, 72 of the jaw assembly 70 could also be plated, sputtered, photo-etched, acid-etched, and/or plasma coated to control the roughness of the surface. The surface or surfaces of the endoscopic instrument may have a roughness in the range of a few hundred microinches, and may be varied, for example, by increments of a few hundred microinches. The relative roughness of the surface or surfaces of the endoscopic instrument may be varied with respect to each other. For example, one surface or portion of a surface may have a relatively rough finish, while another surface or portion of a surface may have a relatively smooth finish.

Providing surface(s) of a medical device, or portions thereof, with a controlled finish, for example a roughened surface, may apply to other types of end effectors or other parts of endoscopic or non-endoscopic instruments, including, but not limited to graspers, scissors, forceps, or other laproscopic, endoscopic, or other devices. Furthermore, other portions of the end effector assembly, including tang portions, clevis portions, and/or axle portions may include surfaces with a controlled finish, for example, a roughened surface. Additionally, only specific portions of parts of the end effector assembly may have a controlled finish. For example, only the inner surfaces of a the jaws of an end effector assembly may have a roughened surface.

Figure 8A:
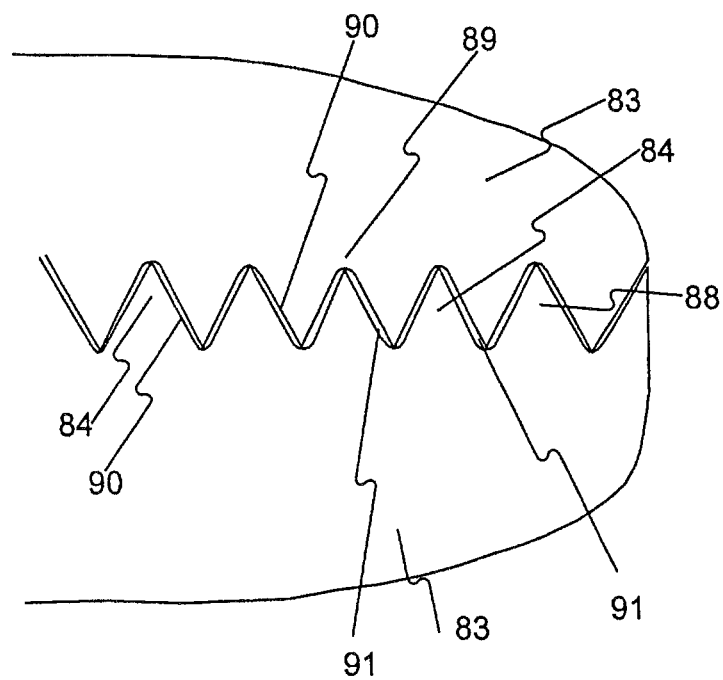
FIG. 8A is a side view of mated jaw portions of an endoscopic instrument.
Figure 8B:
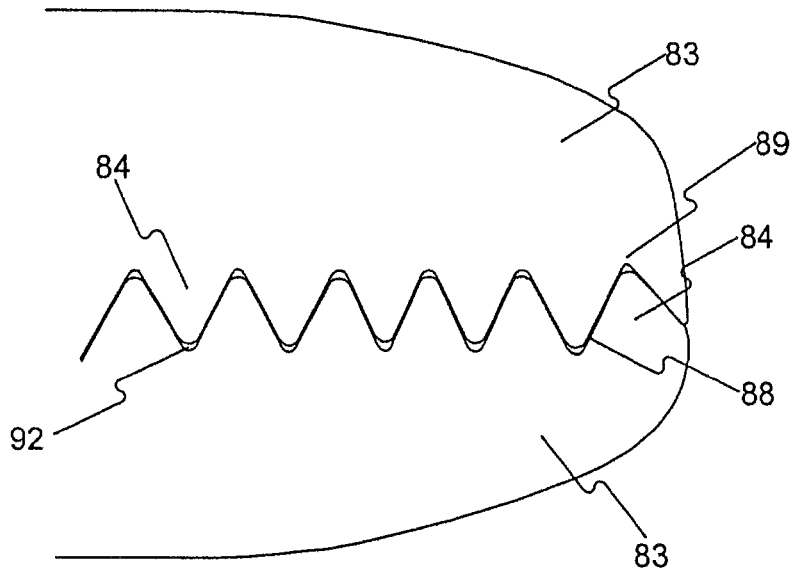
FIG. 8B is a side view of mated jaw portions of an endoscopic instrument.

Views of mated jaw portions 83 of endoscopic instruments are shown in FIGS. 8A and 8B. Each jaw portion 83 has teeth 84, with each tooth 84 having a crest portion 88. A root portion 89 is disposed between each set of adjoining teeth 84. Substantially diagonal portions 90 of the teeth 84 are disposed between the crest 88 and the root 89 to form the tooth.

The configuration of the root 89 may limit the configuration of the teeth. For example, in order for opposing teeth 84 to fit together, the substantially diagonal portions 90 of teeth 84 on opposing jaw portions 83 need to meet before the crest 88 contacts the root 89. Otherwise, a gap 91 will form between the substantially diagonal portions 90 of opposing jaw portions 83, as shown in FIG. 8A. The gap 91 may prevent the opposing jaw portions 83 and teeth 84 from performing an effective cutting action. Though FIG. 8A includes jaws 83 having teeth 84 with sharp tips to enhance biting action, it may be difficult to fabricate jaws (such as through stamping) that have matching sharp-cornered roots 89.

In some cases, to ensure the opposing jaws portions 83 fully close, as shown in FIG. 8B, the crest portion 88 may be given a radius (about 0.005 inches) slightly larger than the radius of the root portion 89 (such as about 0.003 inches). A gap 92 is formed between the crest portion 88 of one jaw portion 83 and the root portion 89 of an opposing jaw portion 83. However, this jaw configuration includes teeth with non-sharp tips (i.e. crests) inhibiting optimal cutting performance.

Figure 6:
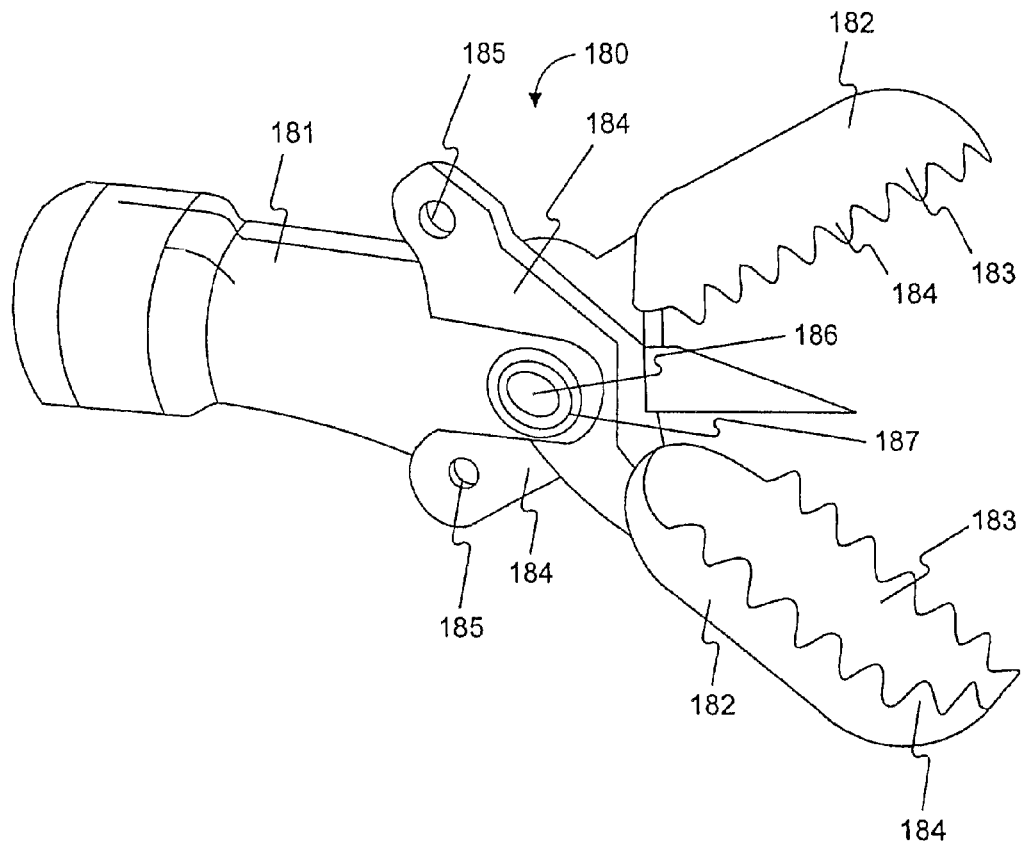
FIG. 6 is a perspective view of a jaw assembly of an endoscopic instrument according to an embodiment of the present invention.
Figure 7:
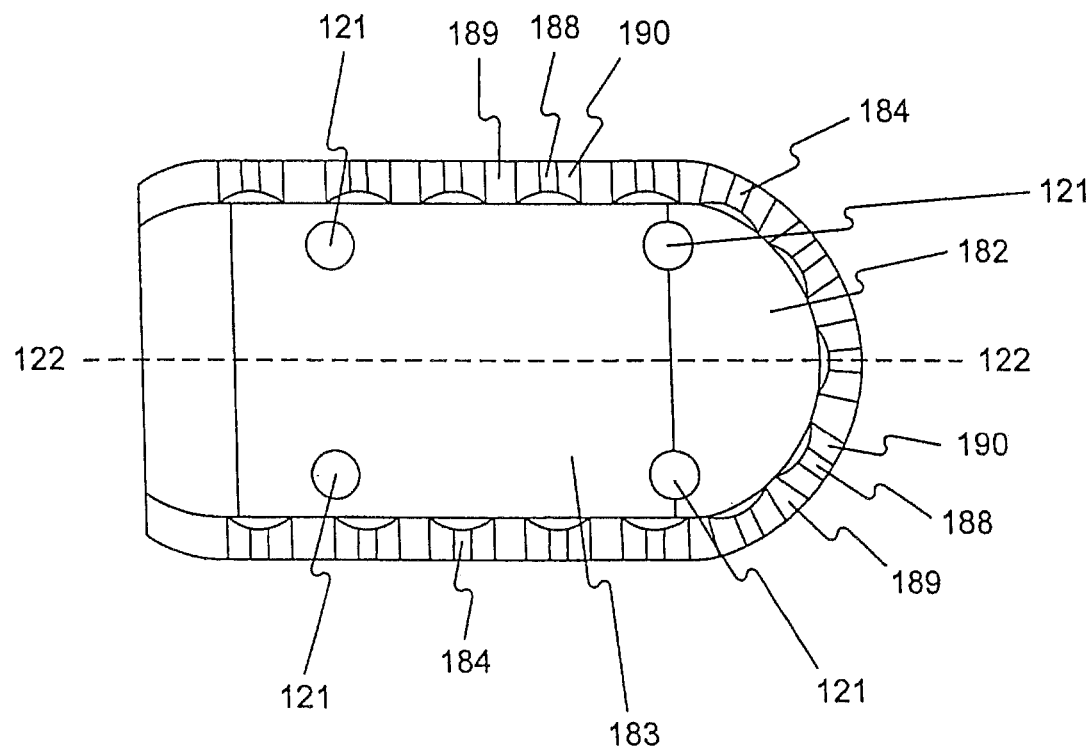
FIG. 7 is a view of a jaw portion of the jaw assembly of FIG. 6.
Figure 9:
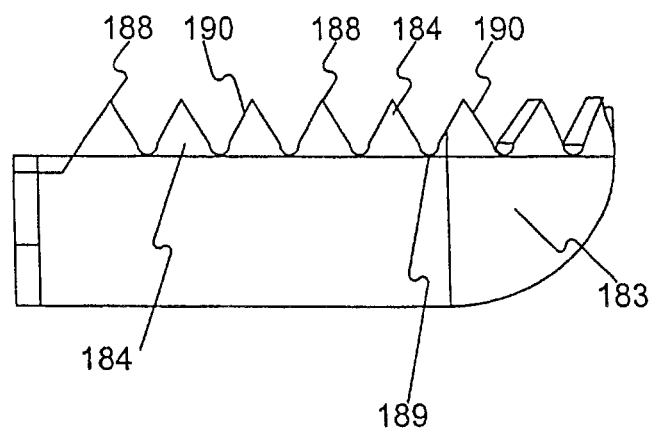
FIG. 9 is a side view of a jaw portion of the jaw assembly of FIG. 6.
Figure 10:
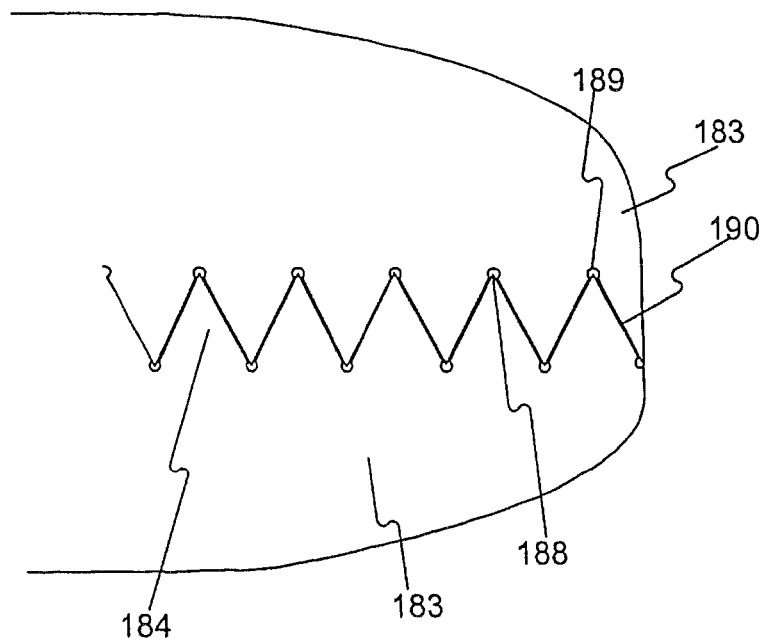
FIG. 10 is a side view of the mated jaw portions of FIG. 9.

Embodiments of the invention include a medical device having jaws with various tooth and/or teeth configurations that overcome one or more of the drawbacks. A jaw assembly 180 according to an exemplary embodiment of the invention is depicted in FIGS. 6, 7, and 9. The jaw assembly 180 includes a clevis 181 configured to be connected to the end of an elongate member 13. Opposing jaws 182 are rotatably attached to the distal end of the clevis 181. Each jaw 182 has a jaw portion 183 connected to a tang portion 184 with mounting holes 185 on the proximal end of the tang portion 184. The holes 185 may be configured to receive and/or retain a wire 15 or other interface device via the clevis 181. Each tang portion 184 also has an axle hole 186 configured to receive an axle 187 that may be connected to the clevis 181. Each jaw portion 183 has a plurality of teeth 184 configured to mate with the plurality of teeth 184 disposed on an opposing jaw portion 183. Material may be removed from the root 189 of adjoining teeth 184 so that, for example, sharper teeth (i.e., crest portions with smaller or no radii) may be used. As shown in FIG. 9, the root 189 has a circular cutout below the point where the crest 188 of an opposing jaw portion 183 would be captured, regardless of the sharpness of the crest 188 (i.e., the crest 188 may have a substantially zero radius). An example of such a configuration is depicted in FIG. 10. Accordingly, the crest 188 may be as sharp as desired, while still allowing the substantially diagonal portions 190 of opposing jaw portions 183 to come into contact with each other. Methods of sharpening teeth 184 such that the crest 188 has a substantially zero radius are known in the art (e.g., stamping, filing, casting). This jaw portion 183 configuration is advantageous as a sharper crest 188 results in a sharper tooth with an improved bite performance.

Figure 11:
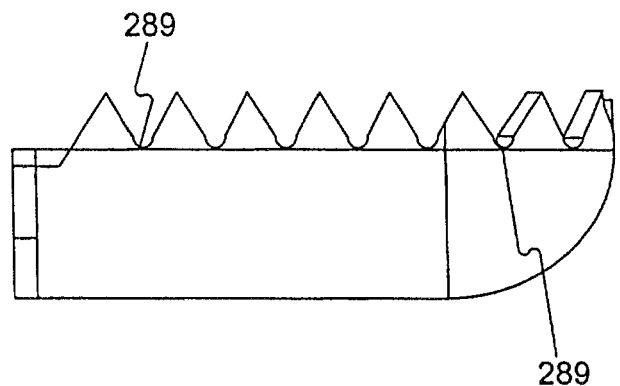
FIG. 11 is a side view of a jaw portion of an endoscopic instrument according to another embodiment of the present invention.
Figure 12:
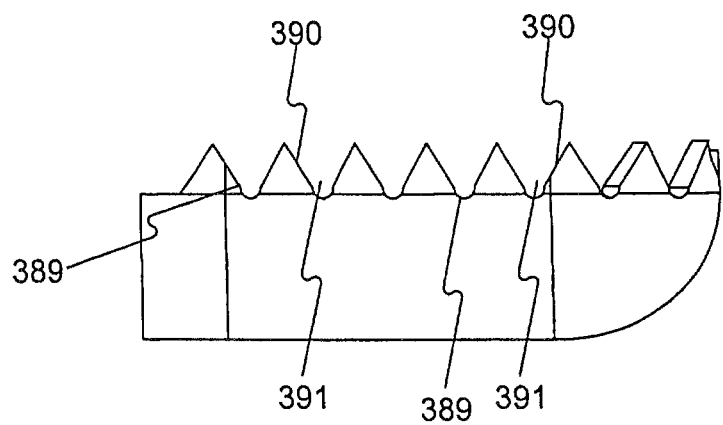
FIG. 12 is a side view of a jaw portion of an endoscopic instrument according to yet another embodiment of the present invention.

In various embodiments, the cutout portions of the root may have any, shape or configuration that permits contact between substantially diagonal portions of opposing jaws that include sharp teeth. For example, FIG. 11 shows a root 289 configuration where the cutout is substantially U-shaped. In another example, FIG. 12 shows a root 389 configuration where the circular cutout is shifted vertically. Each root 389 has a center 391 that is disposed below the lower end of the substantially diagonal surfaces 390. In yet another example, the root portion and/or the circular cutout may also be shifted horizontally, so long as the substantially diagonal portions of the opposing jaw portions come into contact with each other without crests contacting the corresponding roots. In various embodiments, there may be a gap between the tip of the crest and the root, however, the tip of the crest may also just touch the lowest point of the root.

Figure 13:
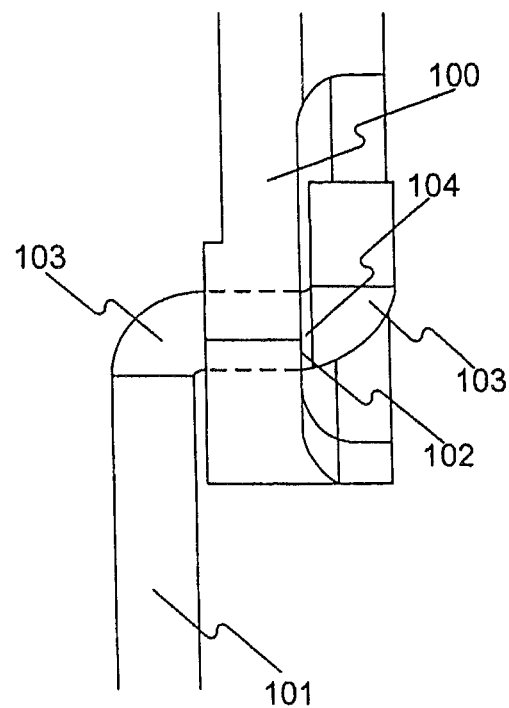
FIG. 13 is a top view of a tang portion and control wire of an endoscopic instrument.

FIG. 13 shows a profile of a tang portion 100 of an end effector assembly for a medical instrument, with a wire 101 disposed in a mounting hole 102 of the tang portion 100. The end portion of the wire 101 has a roughly Z-shaped configuration so as to lodge the wire 101 in the hole 102, allow the wire 101 to rotate with respect to the hole 102, and/or prevent the wire 101 from falling put of the hole 102. The wire end portion has two bends 103 with an interface portion 104 between the bends 103 that contacts the internal surface of the hole 100. The interface portion 104 has substantially the same length as the axial length of the hole 102 and/or the width of the tang 100, for example, to prevent the wire 101 from shifting in the hole 102 and/or falling out of the hole 102. Two methods of forming the roughly Z-shaped configuration (i.e., bends 103) include stamping and/or forging a straight wire 101 into the roughly Z-shaped configuration, however, any method known in the art may be used. If the Z-shape is formed by a stamping or forging operation, the minimum length of the interface portion 104 (i.e., the portion of the wire, between the bends) that may be formed is about 0.015 inches.

Figure 14:
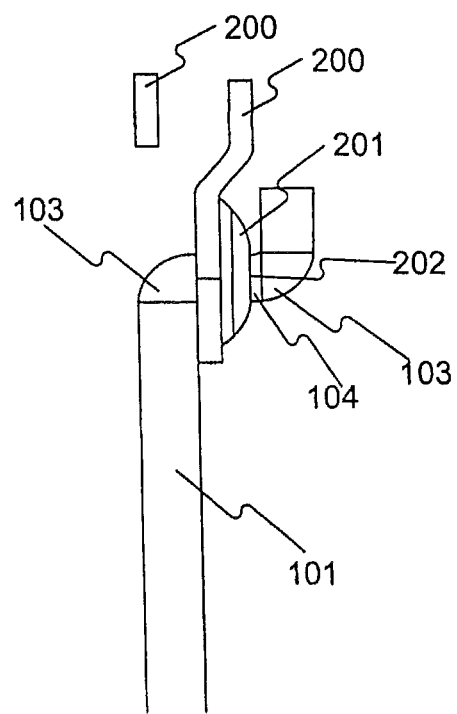
FIG. 14 is a top view of a tang portion and control wire of an endoscopic instrument according to an embodiment of the present invention.

Embodiments of the invention include a medical device having an end effector assembly with various tang configurations. In an exemplary embodiment of the invention, a substantially narrow tang portion may have a widened portion, for example, by placing a dimple 201 on a tang portion 200 around a mounting hole 202. For example, as shown in FIG. 14, the dimple 201 may extend from the surface of the tang portion 200 and increase the width of the tang portion 200. The dimple 201 may be stamped onto the tang portion 200 so as to increase the width of the tang portion 200. This is advantageous because it allows the tang portion 200 and/or the rest of the jaw assembly to have a smaller thickness while still allowing the jaw assembly to accommodate the end portion of the wire 101 set forth above. Specifically, it allows the thickness of the tang portion 200 without the dimple 201 to be reduced, while still allowing the tang portion 200 and/or the mounting hole 202 to receive and accommodate an end portion of a wire 101 with an interface portion 104 having a length of about 0.015 inches. For example, if the width of the tang portion 200 is about 0.007 inches, a dimple 201 of about 0.008 inches could be added to the tang portion 200 so as to accommodate an end portion of a wire 101 with an interface portion 104 having a length of about 0.015 inches, without the end portion of the wire 101 undesirably shifting in and/or falling out of the mounting hole 202. This is especially advantageous when manufacturing a stamped jaw (with tang) having a thickness of material that is less than the length of the interface portion 104.

Figure 15A:
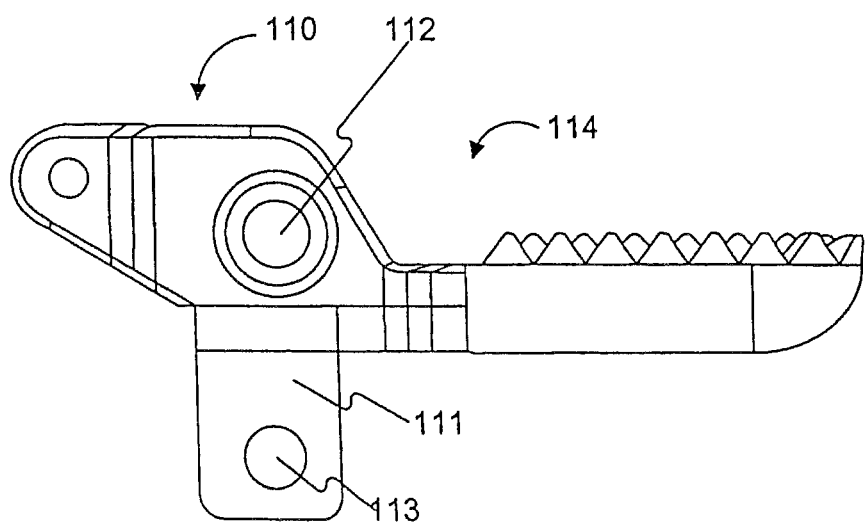
FIG. 15A is a side view of a jaw with a tang portion, having an unfolded additional section, of an endoscopic instrument according to another embodiment of the present invention.
Figure 15B:
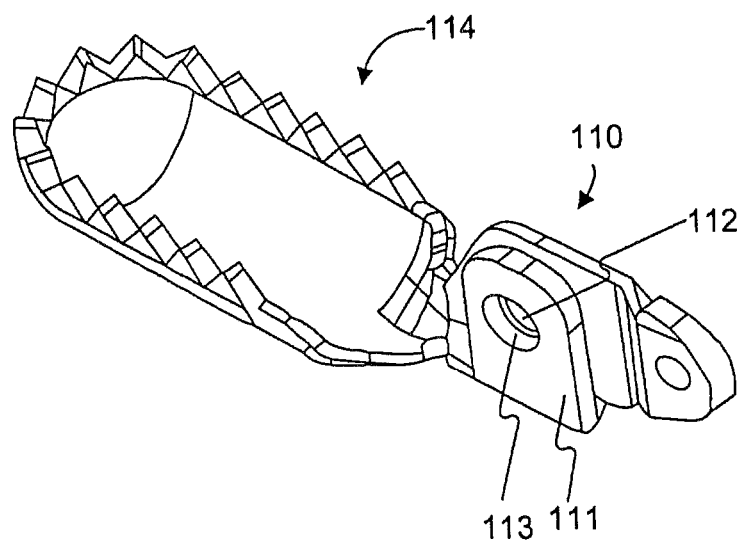
FIG. 15B is a perspective view of the jaw with the tang portion of FIG. 15A, with the additional section folded.

In various embodiments, the bends 103 need not make the end portion of the wire 101 into necessarily a roughly Z-shaped configuration. For example, the bends 103 could form the end portion of the wire 101 into a roughly U-shaped configuration. In addition, the bends 103 may be formed using any method known in the art. Furthermore, the dimples 201 may be formed using any method known in the art. For example, material may be soldered on and/or attached to the tang portion 200 using an adhesive to form dimples 201. Additionally, the thickness of the tang portion need not be increased by placing a dimple, as a portion of the tang portion may be folded over to increase the thickness. For example, in a tang portion manufactured from material having a thickness of about 0.007 inches, folding over the material would create a tang portion with a thickness of about 0.014 inches. FIGS. 15A and 15B described below illustrate this concept as it relates to the axle hole of the jaw. The dimple 201, and/or tang portion 200 may be of any desired shape, size, dimensions, and/or configurations. For example, all the dimensions listed above are exemplary only.

In an exemplary embodiment of the invention, a tang portion of an end effector assembly of a medical device may have a widened and/or thickened portion, for example, by folding over material in a portion of the tang around the axle hole. As shown in FIGS. 15A-15B, a tang portion 110 of an end effector, such as a jaw 114, may be formed such that it has an additional portion 111 extending from the tang portion 110. The additional portion 111 has through hole 113 with substantially the same diameter as an axle hole 112 of the rest of the tang portion 110. The additional portion 111 may then be folded over such that the through hole 113 is aligned with the axle hole 112. For example, a tang portion 110 may be stamped from a material having a thickness of about 0.007 inches. Thus, both the tang portion 110 and the additional portion 111 have a width of about 0.007 inches.

When folded over, the combined width of the tang portion 110 and the additional portion 111 becomes about 0.014 inches. A wider tang portion 110, and particularly a longer axle hole (the combined holes 112 and 113), may be advantageous because it imparts a wider footprint to the jaw mechanism, which may increase the stability and/or precision of the jaw, for example, during the clamping of opposing jaws.

In various embodiments, the tang portion may be widened by forming and then folding over multiple additional portions, for example, three additional portions. The width and/or thickness of other portions of a medical device, including other portions of the end effectors and/or end effector assembly, may be increased using this method. The folded over portion and/or tang portion may be of any desired shape, size, dimensions, and/or configurations. For example, all the dimensions listed above are exemplary only.

In another embodiment of the invention, a tang portion of an end effector assembly of a medical device may have a portion configured to substantially prevent contact between an edge of the end effector and, for example, a tube-like member (such as an endoscope channel) in which the end effector assembly is configured to extend through or other external object. For example, in endoscopic applications, the jaws of a biopsy forceps device will follow the curvature of the endoscope. As the jaws pivot within an endoscope channel, the proximal tang behind the pivot may contact the channel wall. Biopsy jaws, including stamped biopsy jaws, may include sharp edges that may damage the endoscope channel.

Figure 18B:
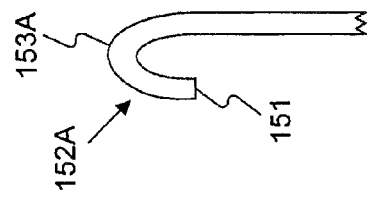
FIG. 18B is a cross-sectional view of the tang portion of FIG. 18A along line 18B-18B.
Figure 18D:
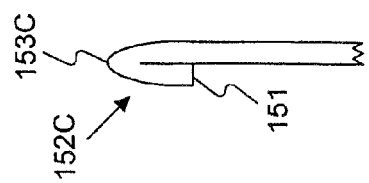
FIG. 18D is a cross-sectional view of a tang portion of a jaw according a yet further embodiment of the present invention.
Figure 18A:
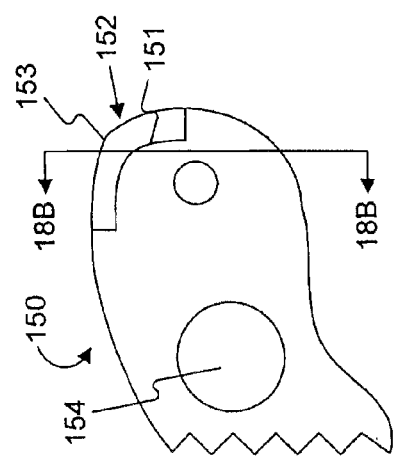
FIG. 18A is a side view of a tang portion of a jaw according to a further embodiment of the present invention.
Figure 18C:
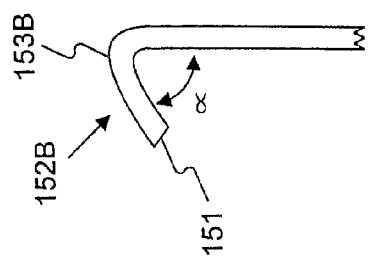
FIG. 18C is a cross-sectional view of a tang portion of a jaw according a still further embodiment of the present invention.

In an exemplary embodiment of the invention, as shown in FIGS. 18A-18D, a portion 152 of the tang 150 may be folded over so as to substantially prevent an edge 151 of the tang 150 from contacting the inside of an endoscope channel. Instead, a, smooth folded portion of the tang having a greater area will contact the endoscope channel. The portion 152 may be disposed on a proximal portion of the tang, however, the portion may also be disposed on any other suitable portion of the end effector. As shown in FIG. 18B, the portion 152A may be curved, however, the portion 152B may also be more sharply folded over as shown in FIG. 18C, or substantially completely folded over as shown in FIG. 18D (i.e., a portion of the folded over portion 152C substantially contacts another portion of the tang 150) so that the portion 152C may be substantially parallel with the tang 150.

The tang 150 may have an outer periphery 153 along its entire circumference. At an apex between the portion 152 and the rest of the tang 150, the outer periphery 153 may be the portion of the tang 150 that comes into contact with the inside of the endoscope channel, for example, as the end effector pivots about a pivot hole 154 of the tang 150. The outer periphery 153A, 153B, 153C at that apex is shown on the respective FIGS. 18B-18D, and preferably has a smooth surface.

In various embodiments, the folded over portion may be folded on any side of the tang and/or may have any desired geometric configuration. For example, the folded over portion may form any desired angle α (see FIG. 18C) with the tang, e.g., more than 90 degrees, less than 90 degrees, and/or substantially 0 degrees. Manufacturing a folded over portion with an angle of more than 90 degrees relative to the remainder of the tang may be easier than manufacturing a folded over portion an angle of less than 90 degrees. However, a folded over portion with a less than a 90 degree angle to the tang may be more effective in substantially preventing contact between a sharp edge of the end effector and the endoscope channel. In examples, the folded over portion may have a substantially rounded shape (e.g., having a constant radius or a variable radius), for example, to present a smooth, non-damaging contact between the tang and the endoscope channel. The folded over portion may have a semi-circular shape of more than 180 degrees, less than 180 degrees, or, substantially equal to 180 degrees. In a further example, the tang may have multiple portions configured to substantially prevent contact between an edge of the end effector and the endoscope channel.

Embodiments of the invention include a medical device with holes in various portions of the medical device, including through the end effectors. For example, as shown in FIG. 7, a jaw 82 of a jaw assembly may have fenestration holes 121 in different portions of jaw 82. Fenestration holes 121 may assist in removing biopsy samples from the jaw 82, for example, by allowing fluid to enter the jaw 82 through the fenestration holes 121, flow between the biopsy sample and the jaw 82, and thus allow the biopsy sample to be flushed out of the jaw 82. The fenestration holes 121 may be disposed off a centerline 122 of the jaw 82. This may be advantageous as when the jaw 82 is placed down a channel, for example the working channel of an endoscope, because the jaw 82 may contact the inner wall of the channel substantially along its centerline 122, the channel will not come into contact with the fenestration holes 121. This may be desirable, for example, because contact between the holes 121 and the channel may cause the holes 121 to catch portions of the channel. This may cause damage to the channel and/or prevent the movement of the medical device with respect to the channel.

In various embodiments, the holes 121 may have any shape, for example, round, circular, oblong, square, and triangular. The holes 121 may also have of any size and have any desired dimensions. There may be any number of holes 121 on any portion of the medical device, but what is disclosed here are holes 121 that are not substantially located on the centerline 122 of the medical device and/or portions of the medical device that may come into contact with a channel and/or another object external to the medical device. The holes 121 need not necessarily be on portions of the medical device that completely preclude the holes 121 from coming into contact with the channel and/or another object external to the medical device, but may be, on a portion where such contact is reduced or minimal relative to other portions of the medical device.

Figure 16:
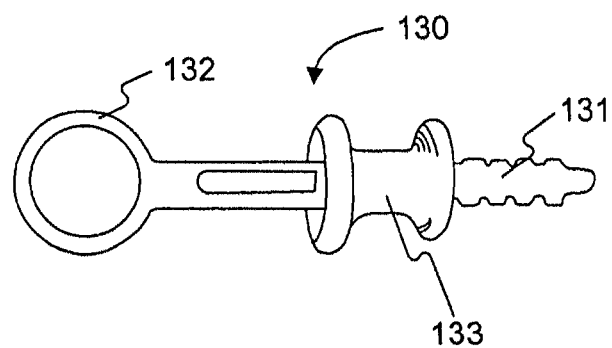
FIG. 16 is a side view of a handle of an endoscopic instrument according to an embodiment of the present invention.
Figure 17:
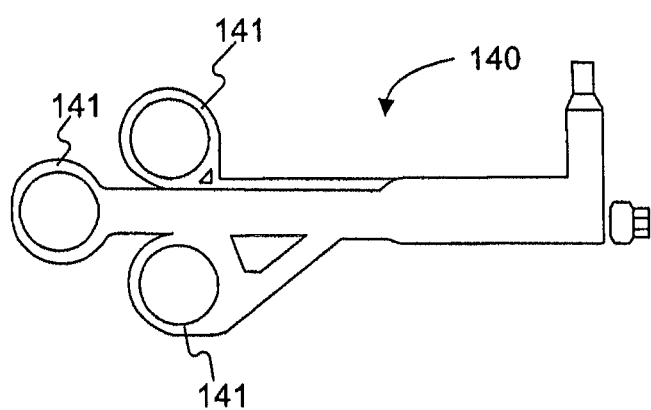
FIG. 17 is a side view of a handle of an endoscopic instrument according to another embodiment of the present invention.

Embodiments of the invention include a medical device with user-interface portions configured to reduce stress (i.e. force) on the operator. For example, the handle of a medical device (e.g., an endoscopic instrument with a handle portion) may have soft-grip features. The entire handle may comprise the soft-grip features, or portions of the handle may have soft grip features, for example, those portions that accommodate a user's fingers. For example, in a handle 130 comprising a ring portion 132, an elongate portion 131, and a spool portion 133 disposed around the elongate portion 131, as shown in FIG. 16, the soft-grip features may be incorporated into the ring portion 132 and/or the spool portion 133. In another example, in a handle 140 comprising three-rings 141, as shown in FIG. 17, the soft-grip features may be incorporated into one or more of the three rings 141. The soft-grip feature may be a low durometer material, for example, santoprene or urethane, incorporated into the medical device. The soft-grip features reduce stress on the operator, for example, by reducing the stress on their hands, and have a more comfortable ergonomic feel. The reduction in stress on the user may allow the user to perform more procedures than with a medical device without the soft-grip features.

In various embodiments, any soft material may be used as soft-grip features, for example, rubber and/or rubbery thermoplastics. The soft-grip features may be placed on any portion of the medical device, for example, that have the potential to be handled by a user, provided that it does not otherwise interfere with the operation of the medical device. The soft-grip features may also be varied across portions of the device: For example, portions of the device may have different materials with different durometers.

Embodiments of the invention include a medical device having portions with variable stiffness. For example, in endoscopic instruments with an elongate member, portions of the elongate member may have variable stiffness. Some portion of the elongate member may be more flexible, for example, to allow the elongate member to be navigated through areas of the body having curves (i.e., tubular regions with greater tortuosity). Because of the flexibility, at least these portions of the elongate member may easily bend around even sharp curves, for example, in the gastrointestinal tract. Other portions of the elongate member may be more rigid, for example, to allow the elongate member to be properly advanced through areas of the body (e.g., tubular regions). Because of the rigidity, at least these portions of the elongate member can be pushed through, for example, the gastrointestinal tract.

Figure 4:
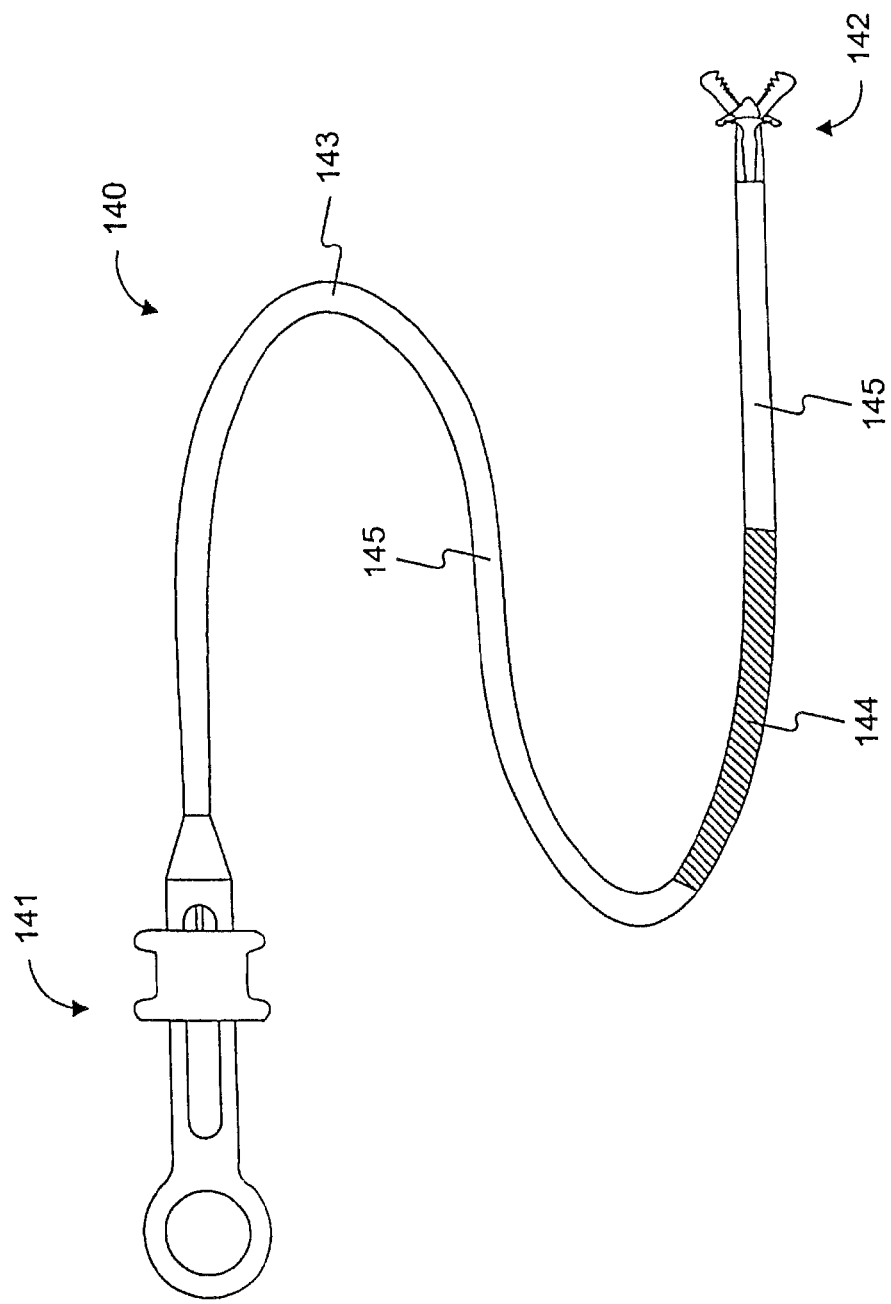
FIG. 4 is a schematic view of an endoscopic instrument with an elongate member of variable flexibility according to an embodiment of the present invention.

In an exemplary embodiment of the present invention, FIG. 4 shows an endoscopic instrument 140 with a handle 141 and an end effector assembly 142 connected by an elongate member 143. The elongate member 143 may have a diameter of about 2.4 mm and a length of about 350 cm. However, any other dimensions suitable for its intended use are also possible. The entire elongate member 143 has a constant strength and feel from its proximal end to distal end, however, a portion 144 of the distal third of the elongate member 143 proximal to the distal end effector assembly has a lower stiffness than the other portions 145 of the elongate member 143. Methods of reducing the stiffness of the desired portion 144 of the elongate member 143 include reducing the diameter of the elongate member 143 in the targeted area, and/or varying the material used in the elongate member 143 such that the lower stiffness portion 144 is comprised of a more flexible material than the higher stiffness portions 145.

In various embodiments, the elongate member may have its rigidity varied along any portion of the elongate member, may have multiple portions with multiple levels of stiffness, and/or may be manufactured using any method known in the art.

Embodiments of the invention include a clevis assembly. An exemplary embodiment of a clevis assembly 300 is shown in FIGS. 19A-19E. The clevis assembly 300 may include an axle 310 and a clevis 320.

The axle 310 may be generally elongate in shape and configured to be used with clevis 320. The axle 310 may have a central portion 311 disposed between ends 312, 313. The central portion 311 may be substantially cylindrical in shape and may be configured to be placed through a hole 321 on one of the arms 322 of the clevis 320. The central portion 311 may also be configured to accommodate a portion of an end effector assembly, such as the proximal tang portions of biopsy jaws.

One end 313 of the axle 310 may be configured to prevent the end 313 from being placed through the hole 321 on the clevis arm 322. The end 313 may include an enlarged head with a shoulder. The head may be substantially hemispherical in shape, however, the end 313 may also have any suitable shape or configuration to prevent its extension through the hole 321.

The end 312 may be substantially round in shape, and may have a groove 314 that separates the end 312 from the central portion 311. The groove 314 may extend all the way around the axle 310, and may be configured to receive a portion of one or more of the protrusions, or cantilever arms, 323 extending around a hole 326 defined by another clevis arm 324.

The clevis 320 may have a base 325 from which arms 322, 324 extend. The arms 322, 324 may be substantially similar in shape, however, they may also have different shapes or configurations. One arm 322 has hole 321 configured to accommodate a portion of axle 310, for example, the central portion 311 of axle 310. Another arm 324 has a hole 326 with a non-uniform edge 327 that is defined by one or more protrusions 323. The protrusions 323 may each have substantially the same shape, or may have different shapes and/or configurations (e.g., spacing). The holes 321, 326 may be substantially coaxial. The portion of the arm 324 defining the hole 326 may be configured to bend or deflect as axle 310 is placed through the hole 326. For example, as shown in FIG. 19E, the protrusions 323 may deflect away from the arm 322 as end 312 of the axle 310 is placed through the hole 326. The portion of the arm 324 defining the hole 326 may also be configured to substantially return to its original configuration. For example, once the end 312 of the axle 310 has been placed through the hole 326 a suitable amount, the protrusions 323 may deflect or spring back toward the arm 322 and at least a portion of the protrusions 323 may become lodged in groove 314.

The portion of the arm 324 not defining the hole 326 and/or protrusions 323 may be configured to be rigid enough such that the arm 324 does not substantially bend or deflect while the protrusions 323 bend or deflect as the end 312 of the axle 310 is placed through the hole 326. For example, the portion of the arm 324 not defining the hole 326 may be thicker than the protrusions 323. The base 325 may also be configured to be more rigid than the arms 322, 324, for example, so as to not substantially bend or deflect while the protrusions 323 may bend or deflect as the end 312 of the axle 310 is placed through the hole 326. In another example, the portion of the arm 324 not defining the hole 326 and/or protrusions 323 may not have any particular configuration or rigidity such that the arm 324 does not substantially bend or deflect while the protrusions 323 bend or deflect as the end 312 of the axle 310 is placed through the hole 326. For example, arm 324 may simply have roughly the same thickness, rigidity, and/or metallic properties as the rest of the clevis assembly 300. In such cases, tooling may be used to prevent deflection of the arm 324. For example, the arm 324 may be placed between grippers, vices, or any other suitable tooling known in the art so as to substantially prevent deflection of the arm 324 in a direction substantially perpendicular to the surface of the arm 324 and/or substantially parallel to the longitudinal axis of the axle 311 (e.g., when the end 312 of the axle 310 is placed through the hole 326 and exerts force on the protrusions 323).

Another exemplary embodiment of a clevis assembly 400 is shown in FIGS. 20A-20C. The clevis assembly 400 may include an axle 410 and a clevis 420.

The axle 410 may have two ends 411, 412 disposed around a central portion 413. The central portion 413 may be substantially cylindrical in shape and may be configured to be disposed in holes 421, 422 on arms 423, 424 on the clevis 420. The central portion 413 may also be configured to accommodate a portion of an end effector assembly, such as the proximal tang portions of biopsy jaws.

The ends 411, 412 may have a generally rounded shape and may be configured to prevent the ends 411, 412 from being placed through at least one of the holes 421. For example, the ends 411, 412 may include an enlarged head and a shoulder. The head may, be substantially hemispherical in shape, however, the ends 411, 412 may have any suitable shape or configuration. An inner surface 414, 415 of the ends 411, 412 may be configured to prevent the rest of the end 411, 412 from being placed through holes 421, 422. An outer surface 416, 417, however, may be configured to be placed through at least one of the holes 421, 422. The ends 411, 412 may have substantially the same shape and configuration, or may have different shapes and/or configurations. For example, one of the ends 411, 412 may be configured so that it may not be placed through at least one of the holes 421, 422.

The clevis 420 may have a base 425 from which arms 423, 424 extend. The arms 423, 424 may have substantially similar shapes, or may have different shapes and/or configurations. One or more of the arms 423, 424 may define a hole 421, 422 with one or more protrusions 426A, 426B adjacent portions of the hole 421, 422. The protrusions 426A, 426B may have the same shape, or may have different shapes. The protrusions 426A, 426B may define substantially rounded inner edges 427 that are configured, for example, to define portions of a circle. The protrusions 426A may be configured to deflect toward arm 424 as end 411 is placed through the hole 421. The protrusions 426B may be configured to deflect away from arm 423 as end 411 is placed through the hole 422. As shown in FIG. 20C, when an outer surface 416 of an end 411 of an axle 410 is pressed against the protrusions 426B, the protrusions 426B may deflect as the end 411 is advanced through hole 422. Once the end 411 has suitably advanced through the hole 422, the protrusions 426B may reversibly deflect toward the arm 423 such that the inner edges 427 are adjacent an outer surface of the central portion 413. In such a configuration, the inner surfaces 414, 415 of the ends 411, 412 may be adjacent outer surfaces of the arms 423, 424. The same may substantially be true for hole 421 and protrusions 426A, except that the outer surface 416 of the end 411 of the axle 410 may first come into contact with an outer surface of arm 423, and the protrusions 426A may deflect inward (i.e., toward arm 424).

The portion of the arm 423, 424 not defining the hole 421, 422 and/or protrusions 426A, 426B may be configured to be rigid enough such that the arm 423, 424 does not substantially bend or deflect while the protrusions 426A, 426B may bend or deflect as the end 411 of the axle 410 is placed through the hole 421,422. For example, the portion of the arm 423, 424 not defining the hole 421, 422 may be thicker than the protrusions 426A, 426B. The base 425 may also be configured to be more rigid than the arms 423, 424, for example, so as to not substantially bend or deflect while protrusions 426A, 426B may bend or deflect as the end 411 of the axle 410 is placed through the hole 421, 422. In another example, the portion of the arm 423, 424 not defining the hole 421, 422 and/or protrusions 426A, 426B may not have any particular configuration or rigidity such that the arm 423, 424 does not substantially bend or deflect while the protrusions 426A, 426B bend or deflect as the end 411 of the axle 410 is placed through the hole 426A, 426B. For example, arms 423, 424 may have roughly the same thickness, rigidity, and/or metallic properties as the rest of the clevis assembly 420. In such a case, tooling may be used to prevent deflection of the arm 423, 424. For example, the arm 423, 424 may be placed between grippers, vices, or any other suitable tooling known in the art so as to substantially prevent deflection of the arm 423, 424 in a direction substantially perpendicular, to the surface of the arm 423 424 and/or substantially parallel to the longitudinal axis of the axle 410 (e.g., when the end 411 of the axle 410 is placed through the hole 421, 422 and exerts force on the protrusions 426A, 426B).

In various embodiments, each arm of the clevis may define a hole with protrusions configured to deflect and then return to its original configuration as an axle is placed therethrough, substantially as set forth above. However, in other embodiments, clevis arms may have different configurations. For example, one of the arms may define a hole with protrusions configured to deflect and then return to its original configuration as an axle is placed therethrough, however, the other arm may define a hole without protrusions that is otherwise configured to allow an end of an axle to pass through the hole without substantially deflecting any portion of the arm. In such a configuration, one end of the axle may have a small enough size and/or shape to pass through the hole on one of the arms and then deflect the protrusions adjacent the hole on the other arm as the end passes therethrough.

There may be several advantages to having a clevis assembly with an axle and clevis configuration according to one of the embodiments set forth herein, for example, FIGS. 19A-19E and 20A-20C. One advantage is the elimination of a rivet and the use of expensive riveting equipment to manufacture the clevis assembly. Another advantage is that the clevis assembly may be assembled quickly and through an automated process. A further advantage is that the axle may be solid and thus less expensive than hollow axles which may be used in other clevis assembly configurations. Yet another advantage is that the axle may not include sharp points or edges that may damage the walls of a working channel of an endoscope through which the clevis assembly may be placed. Still another advantage is that the groove may be accurately and precisely placed on the axle such that when the clevis assembly is assembled and the protrusions on the hole of one of the arms are disposed in the groove, the resulting distance between the arms may be precisely controlled and/or ideally manufactured for the intended use of the clevis assembly.

In various embodiments, all aspects of the invention set forth herein may be used in conjunction with any medical device, instrument, or procedure, and/or any non-medical device, instrument, or procedure. In addition, one or more of the aspects of the invention set forth herein may be combined in the same device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A jaw assembly for an end effector assembly of a medical device, comprising:
    a jaw, including an arcuate body section and a rim section,
        the body section being positioned below the rim section in a first direction perpendicular to a plane extending from a proximal end to a distal end of the rim section; and
    a tang extending from the jaw, the tang including a first arm and a second arm each having a first hole therein, wherein the first arm includes a second hole therein, and the first holes of the first and second arms are the proximal-most holes on the first and second arms and are off-axis from each other, wherein an axis passes through a center of each of the first hole of the second arm and the second hole of the first arm, and a first plane passes through the center of each of the first hole of the second arm and the second hole of the first arm and is perpendicular to the first arm and the second arm, and wherein the first arm connects to the second arm by material positioned below the axis in the first direction, transverse to the first plane, and between second and third planes defining the first and second arms respectively, and wherein the second arm has a first edge that is connected to the material that connects the first arm to the second arm and a free distal-most edge;
    wherein the distal end of the rim section is disposed remote from the tang and has a plurality of teeth projecting above the plane of the rim section, and the proximal end of the rim section is disposed adjacent the tang and is void of teeth.

2. The jaw assembly of claim 1, wherein the arcuate body section includes a plurality of through-holes therein.

3. The jaw assembly of claim 2, wherein the plurality of through-holes in the arcuate body section are disposed off of a centerline of the jaw.

4. The jaw assembly of claim 1, wherein the first arm of the tang is connected to the second arm of the tang forming a substantially U-shaped tang.

5. The jaw assembly of claim 1, wherein the plurality of teeth includes a plurality of crests interspaced between a plurality of roots, and a plurality of intermediate portions disposed between a respective crest and a respective root.

6. The jaw assembly of claim 5, wherein each of the plurality of roots includes at least a partial, substantially circular shape.

7. The jaw assembly of claim 1, wherein the first arm of the tang is fixed relative to the jaw, and the second arm of the tang is moveable relative to the jaw.

8. The jaw assembly of claim 1, wherein the first arm of the tang and the jaw are a single piece of material.

9. The jaw assembly of claim 1, wherein a proximal-most edge of the second arm is free.

10. An end effector for a medical device, comprising:
    a first jaw and a second jaw;
    wherein the first and second jaws each include:
    a tang including a first arm and a second arm each having a first hole therein, wherein the first arm includes a second hole therein, and the first holes of the first and second arms are off-axis from each other,
    an arcuate body section and a rim section, the body section having an open portion defining the rim section, wherein the body section extends from the rim section in a direction perpendicular to a plane extending from a proximal end to a distal end of the rim section, the rim section including:
        the distal end, disposed remote from the tang, having a plurality of teeth projecting from the plane of the rim section, and
        the proximal end, disposed adjacent the tang, being void of teeth,
    wherein an axis passes through a center of each of the first hole of the second arm and the second hole of the first arm, and for the first jaw, the first arm connects to the second arm by material positioned below the axis in the direction and between first and second planes defining the first and second arms respectively, and wherein a distal end of the second arm of the first jaw is free and does not contact the body section of the first jaw, and for the second jaw, the first arm connects to the second arm by material positioned above the axis in the direction and between first and second planes defining the first and second arms respectively, and wherein a distal end of the second arm of the second jaw is free and does not contact the body section of the second jaw; and for each of the first jaw and the second jaw, a third plane passes through the center of each of the first hole of the second arm and the second hole of the first arm, and the material intersects and is perpendicular to the third plane.

11. The end effector of claim 10, wherein the arcuate body section of each of the first and second jaws includes a plurality of through-holes therein.

12. The end effector of claim 10, wherein for each of the first and second jaws, the first hole of the first arm is spaced from the first hole of the second arm.

13. The end effector of claim 12, wherein for each of the first and second jaws, the first arm of the tang is connected to the second arm of the tang to form a substantially U-shaped tang.

14. The end effector of claim 10, wherein the plurality of teeth of each of the first and second jaws includes:
a plurality of crests interspaced between a plurality of roots, and
a plurality of intermediate portions disposed between a respective crest and a respective root.

15. The end effector of claim 14, wherein each of the plurality of roots includes at least a partial, substantially circular shape.

16. The end effector of claim 14, wherein:
each of the crests of the plurality of teeth on the first jaw and each of the crests of the plurality of teeth on the second jaw includes a pointed tip; and
each of the roots of the plurality of teeth on the first jaw and each of the roots of the plurality of teeth on the second jaw includes a rounded shape for accommodating the crest of an opposing tooth such that a gap exists between the crest of one tooth and the lowest point of one root when the first and second jaws are fully closed.

17. A medical device, comprising:
a shaft;
a handle attached to a proximal end of the shaft; and
an end effector assembly attached to a distal end of the shaft, the end effector including a first jaw and a second jaw;
wherein the first jaw includes (i) a tang including a first arm and a second arm, each of the first and second arms having a first hole therein, wherein the first arm includes a second hole therein, and the first holes of the first and second arms are the proximal-most holes on the first and second arms and are off-axis from each other, and (ii) a jaw having an arcuate body section and a rim section, the rim section including a distal end, disposed remote from the tang, having a plurality of teeth, a proximal end, disposed adjacent the tang, being void of teeth, and the body section being positioned below the rim section in a first direction perpendicular to a plane extending from the proximal end to the distal end of the rim section, wherein an axis passes through a center of each of the first hole of the second arm and the second hole of the first arm, wherein the first arm connects to the second arm by material positioned below the axis in the first direction and between planes defining the first and second arms and wherein a plane passes through the center of each of the first hole of the second arm and the second hole of the first arm, and the material intersects and is perpendicular to the plane through the center of each of the first hole of the second arm and the second hole of the first arm, and wherein a distal end of the second arm is free and is not directly connected to the body section of the first jaw; and wherein the second jaw includes (i) a second tang including a third arm and a fourth arm, each of the third and fourth arms having a third hole therein, wherein the third arm includes a fourth hole therein, and the third holes of the third and fourth arms are the proximal-most holes on the third and fourth arms and are off-axis from each other, and (ii) a jaw, having a second arcuate body section and a second rim section, the second rim section including a distal end, disposed remote from the second tang, having a plurality of teeth, a proximal end, disposed adjacent the second tang, being void of teeth, and the second body section being positioned above the second rim section in a second direction perpendicular to a plane extending from the proximal end to the distal end of the second rim section, wherein a second axis passes through a center of each of the third hole of the fourth arm and the fourth hole of the third arm, wherein the third arm connects to the fourth arm by material positioned above the second axis in the second direction and between planes defining the third and fourth arms and wherein a plane passes through the center of each of the third hole of the fourth arm and the fourth hole of the third arm and the material intersects and is perpendicular to the plane passing through the center of each of the third hole of the fourth arm and the fourth hole of the third arm, and wherein a distal end of the fourth arm is free and is not directly connected to the body section of the second jaw.

18. The medical device of claim 17, wherein the plurality of teeth of each of the first and second jaws includes:
a plurality of crests interspaced between a plurality of roots, and
a plurality of intermediate portions disposed between a respective crest and a respective root.

19. The medical device of claim 18, wherein:
each of the crests of the plurality of teeth on the first jaw and each of the crests of the plurality of teeth on the second jaw includes a pointed tip; and
each of the roots of the plurality of teeth on the first jaw and each of the roots of the plurality of teeth on the second jaw includes a rounded shape.

* * * * *